(12) United States Patent
Weissbrich

(10) Patent No.: US 11,129,872 B2
(45) Date of Patent: Sep. 28, 2021

(54) METHODS OF MAKING AND USING SOLUBLE MHC MOLECULES

(71) Applicant: Kite Pharma, Inc., Santa Monica, CA (US)

(72) Inventor: Bianca Weissbrich, Amsterdam (NL)

(73) Assignee: Kite Pharma, Inc., Santa Monica, CA (US)

( * ) Notice: Subject to any disclaimer, the term of this patent is extended or adjusted under 35 U.S.C. 154(b) by 662 days.

(21) Appl. No.: 15/674,815

(22) Filed: Aug. 11, 2017

(65) Prior Publication Data

US 2018/0042995 A1    Feb. 15, 2018

Related U.S. Application Data

(60) Provisional application No. 62/373,695, filed on Aug. 11, 2016.

(51) Int. Cl.
| | |
|---|---|
| C07K 14/74 | (2006.01) |
| G01N 33/532 | (2006.01) |
| G01N 33/533 | (2006.01) |
| G01N 33/534 | (2006.01) |
| A61K 38/17 | (2006.01) |
| A61K 39/385 | (2006.01) |
| C07F 9/50 | (2006.01) |
| G01N 33/569 | (2006.01) |
| A61K 39/00 | (2006.01) |
| C07K 14/705 | (2006.01) |

(52) U.S. Cl.
CPC ........ *A61K 38/1774* (2013.01); *A61K 39/385* (2013.01); *C07F 9/50* (2013.01); *C07K 14/70539* (2013.01); *G01N 33/532* (2013.01); *G01N 33/56972* (2013.01); *A61K 2039/5158* (2013.01); *C07K 14/705* (2013.01); *C07K 2319/00* (2013.01); *G01N 2333/7051* (2013.01); *G01N 2333/70539* (2013.01); *G01N 2500/04* (2013.01)

(58) Field of Classification Search
None
See application file for complete search history.

(56) References Cited

U.S. PATENT DOCUMENTS 10,369,204 B2 *  8/2019  Scholler ................. A61K 39/12

FOREIGN PATENT DOCUMENTS

WO           99/11775 A1     3/1999

OTHER PUBLICATIONS

Rodenko et al (Nature Protocols, 2006, 1(3): 1120-132) (Year: 2006).*
HLA Nomenclature 2015 (Year: 2015).*
Toebes et al (Nat. Med. 2006, 12(2): 246-251) (Year: 2006).*
Rodenko et al (J. Amer. Chem. Soc. 2009, 131: 12305-12313) (Year: 2009).*
Parker et al (J. Immunol. 1994, 152: 163-175) (Year: 1994).*
Amore et al (ChemBioChem, 2013, 14: 123-131) (Year: 2013).*
Leriche et al (Bioorganic & Med. Chem. 2012, 20: 571-582) (Year: 2012).*
DiBrino et al (J. Immunology 151(11) 5390-5935, 1993) (Year: 1993).*
Engelhard, V.H., Curr. Opin. Immunol. 1994, 6: 13-23) (Year: 1994).*
Guo et al (Nature, 1992, 360: 364-366) (Year: 1992).*
Weibrich, B.; T cell Receptor Binding Avidity of Antigen-Specific CD8 + Cytotoxic T cells in Chronic Infection, Nov. 18, 2015 (Nov. 18, 2015), pp. 1-150, XP055414369; Munchen, URL:https://mediatum.ub.tum.de/doc/1254464/1254464.pdf, p. 53, paragraph 2—p. 68, last paragraph p. 90-p. 91; figures 4-40,4-41.
Nauerth, M.; Development of a Novel TCR Avidity Assay for Human CD8+ TCells, Jan. 1, 2012 (Jan. 1, 2012), URL:http://mediatum.ub.tum.de/doc/1097838/ 1097838.pdf, XP055308572.
Rodenko Bet Al: "Generation of peptide-MHC class I complexes through UV-mediated ligand exchange", Nature Protocols, Nature Publishing Group, GB, vol. 1, No. 3, Jan. 1, 2006 (Jan. 1, 2006) pp. 1120-1131,XP003027415; ISSN: 1750-2799, DOI: 10.1038/NPROT.2006.121;.
European Patent Office, Annex to Form PCT/ISA206 Communication Relating to the Results of the Partial International Search in International Application No. PCT/EP2017/070460, dated Dec. 18, 2017.
Owen, J. A., et al., Kuby Immunology, 7th Edition, 2012, W. H. Freeman and Company • New York.
Vigano, S., et al., "Functional Avidity: A Measure to Predict the Efficacy of Effector T Cells?" Clinical and Developmental Immunology, Oct. 22, 2012, vol. 2012, Article ID 153863, 14 pages, doi:10.1155/2012/153863.
Khilko, S. N., et al., "Measuring Interactions of MHC Class I Molecules Using Surface Plasmon Resonance" (1995) Journal of Immunological Methods 183(1): 77-94.
Bridgeman, J. S., et al., "Structural and biophysical determinants of ab T-cell antigen recognition" (2012) Immunology 135(1): 9-18; Blackwell Publishing Ltd.
Campanelli, R., et al., Human CD8 co-receptor is strictly invoilved in MHC-peptide tetramer-TCR binding and T cell activation (2002) International Immunology, vol. 14, No. 1, pp. 39-44, The Japanese Society for Immunology.
Wang, X.L., et al., "Caveats in the design of MHC class I tetramer/antigen-specific T lymphocytes dissociation assays", Journal of Immunological Methods, 280 (2003) 25-35, Elsevier B.V. doi:10.1016/S0022-1759(03)00079-6.

(Continued)

*Primary Examiner* — G. R. Ewoldt
*Assistant Examiner* — Marianne DiBrino
(74) *Attorney, Agent, or Firm* — Sheppard Mullin Richter & Hampton LLP

(57) ABSTRACT

Provided herein are methods of making a detectably-labeled, soluble MHC molecule that can be used in a novel $K_{on}$-rate assay and an improved TCR ligand $k_{off}$-rate assay.

11 Claims, 16 Drawing Sheets

Specification includes a Sequence Listing.

(56) References Cited

OTHER PUBLICATIONS

Stone, Jennifer, et al., Interaction of Streptavidin-Based Peptide-MHC Oligomers (Tetramers) with Cell-Surface T Cell Receptors, J Immunol. Dec. 15, 2011; 187(12): 6281-6290. doi:10.4049/jimmunol.1101734.

Huang, J., et al. "The kinetics of two dimensional TCR and pMHC interactions determine T cell responsiveness", Nature. Apr. 8, 2010; 464(7290): 932-936. doi:10.1038/nature08944.

Huppa, J.B., et al. "TCR—peptide—MHC interactions in situ show accelerated kinetics and increased affinity", Nature. Feb. 18, 2010; 463(7283): 963-967. doi:10.1038/nature08746.

Puench, P.H., et al. , "Force Measurements of TCR/pMHC Recognition at T Cell Surface", Jul. 22, 2011, PLoS ONE 6(7): e22344. doi:10.1371/journal.pone.0022344.

Nauerth M., et al, "TCR-Ligand koff Rate Correlates with the Protective Capacity of Antigen-Specific CD8+ T Cells for Adoptive Transfer", Jul. 3, 2013 (Jul. 3, 2013), Science Translational Medicine, vol. 5, No. 192, 3, pp. 192ra87-192ra87, ISSN: 1946-6234, DOI: 10.1126/scitranslmed.3005958.

Hebeisen, M., et al., "Identification of Rare High-Avidity, Tumor-Reactive CD8β T Cells by Monomeric TCR-Ligand Off-Rates Measurements on Living Cells", Mar. 25, 2015, Cancer Res 75(10):1983-91, DOI: 10.1158/0008-5472. CAN-14-3516, retrieved on Feb. 28, 2018.

Weissbrich, B. et al: "Adoptive immunotherapy New assay for the identification of T cells with optimal avidity", Oncoimmunology, vol. 2, No. 10, Oct. 1, 2013 (Oct. 1, 2013), p. e26199, DOI: 10.4161/onci.26199.

Dossinger, G. et al., "MHC Multimer-Guided and Cell Culture-Independent Isolation of Functional T Cell Receptors from Single Cells Facilitates TCR Identification for Immunotherapy", Apr. 26, 2013, PLoS ONE 8(4): e61384. doi:10.1371/journal.pone.0061384.

Linnemann, C., et al., "High-throughput identification of antigen-specific TCRs by TCR gene capture", Oct. 13, 2013, Nat Med 19(11):1534-1541, doi: 10.1038/nm.3359.

Hamana, H., et al., "A novel, rapid and efficient method of cloning functional antigenspecific T-cell receptors from single human and mouse T-cells", (2016), Biochemical and Biophysical Research Communications 474, pp. 709-714.

Zhang, SQ, et al., "Direct measurement of T cell receptor affinity and sequence from naive antiviral T cells" (2016), Sci Transl Med 8(341), 341ra77.

Pleun Hombrink, et al.; "Mixed functional characteristics correlating with TCR-ligand k off-rate of MHC-tetramer reactive T cells within the naive T-cell repertoire", European Journal of Immunology, vol. 43, No. 11, Nov. 25, 2013 (Nov. 25, 2013), pp. 3038-3050, XP055211633, ISSN: 0014-2980, DOI: 10.1002/eji.201343397.

Magdalena Nauerth, et al.; The clinical potential for k off-rate measurement in adoptive i mmunotherapy, Expert Review of Clinical Immunology, vol. 9, No. 12, Dec. 1, 2013 (Dec. 1, 2013), pp. 1151-1153, XP055211630, ISSN: 1744-666X, DOI: 10.1586/1744666X.2013.855609.

Batard P., et al.; "Dextramers: New generation of fluorescent MHC class I/peptide multimers for visualization of antigen-specific CD8<+> T cells", Journal of Immunological Methods, Elsevier Science Publishers B.V.,Amsterdam, NL, vol. 310, No. 1-2, Mar. 20, 2006 (Mar. 20, 2006), pp. 136-148, XP028017573, ISSN: 0022-1759, DOI: 10.1016/J.JIM.2006.01.006.

Jun Huang, et al.; "Detect ion, phenotyping, and quantification of antigen-specific T cells using a peptide-MHC dodecamer", Proceedings National Academy of Sciences PNAS, vol. 113, No. 13, Mar. 15, 2016 (Mar. 15, 2016), pp. E1890-E1897, XP055349051, US, ISSN: 0027-8424, DOI: 10.1073/pnas.1602488113.

European Patent Office, International Search Report and Written Opinion in International Application No. PCT/EP2017/070460, dated Feb. 19, 2018.

Burmeister Getz et al., "A Comparison between the Sulfhydryl Reductants Tris(2-carboxyethyl)phosphine and Dithiothreitol for Use in Protein Biochemistry," Analytical Biochemistry, 1999, 273:73-80.

Office Action in EP 17758086.7 dated Apr. 23, 2020, 7 Pages.

* cited by examiner

Figure 4A
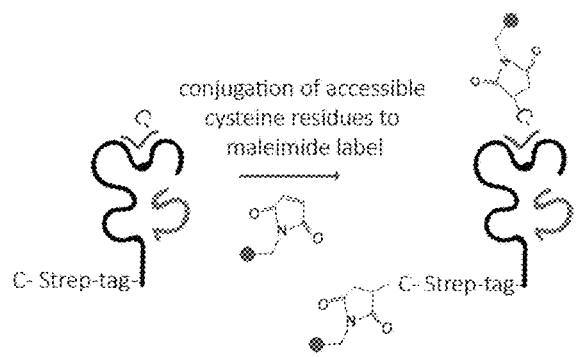
Figure 4B
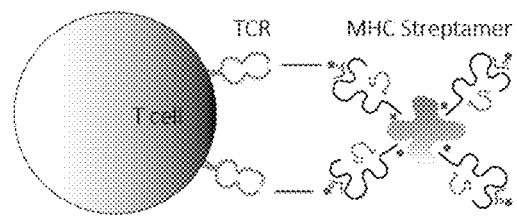
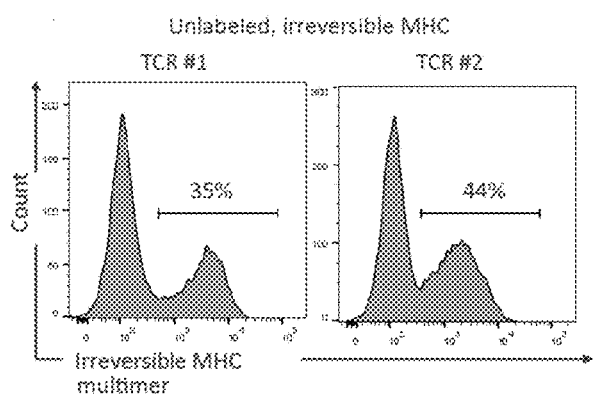
Figure 4C
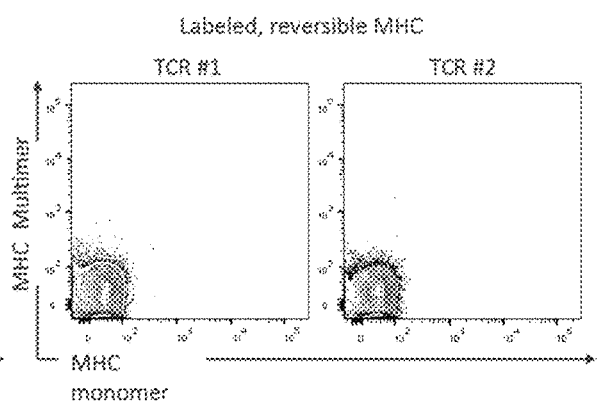
Figure 4D

Figure 7A
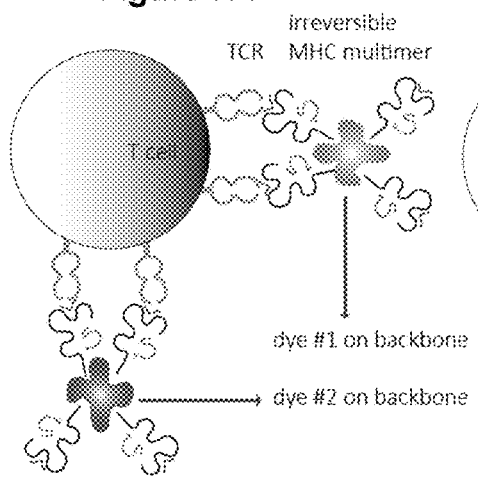
irreversible
TCR MHC multimer
dye #1 on backbone
dye #2 on backbone
Figure 7B
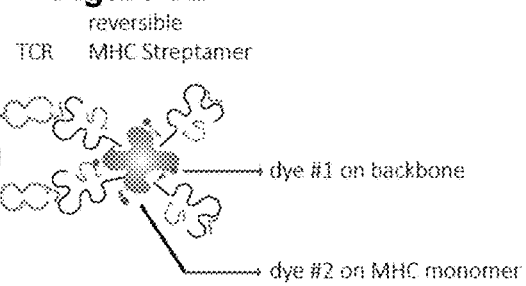
reversible
TCR MHC Streptamer
dye #1 on backbone
dye #2 on MHC monomer
Figure 7C
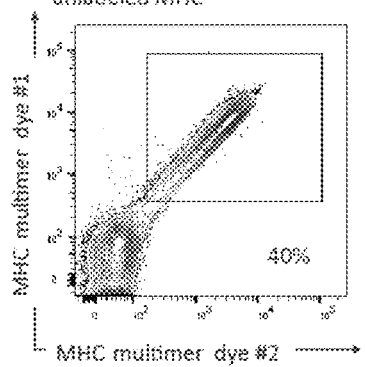
UV-peptide exchanged, unlabeled MHC
MHC multimer dye #1
MHC multimer dye #2
40%
Figure 7D
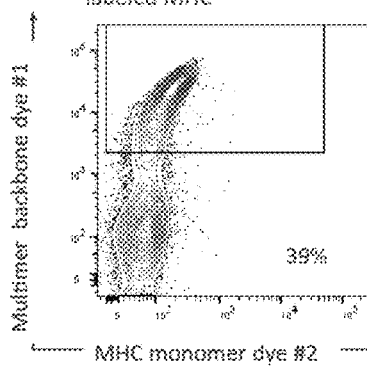
Conventional refolded, labeled MHC
Multimer backbone dye #1
MHC monomer dye #2
39%
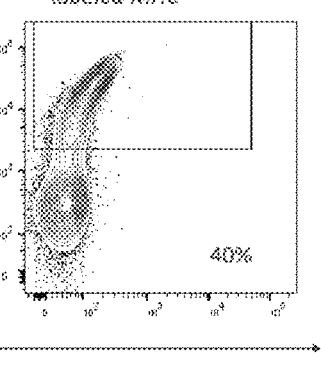
UV-peptide exchanged, labeled MHC
40%
Figure 7E Figure 8A
Conventional refolded, labeled MHC
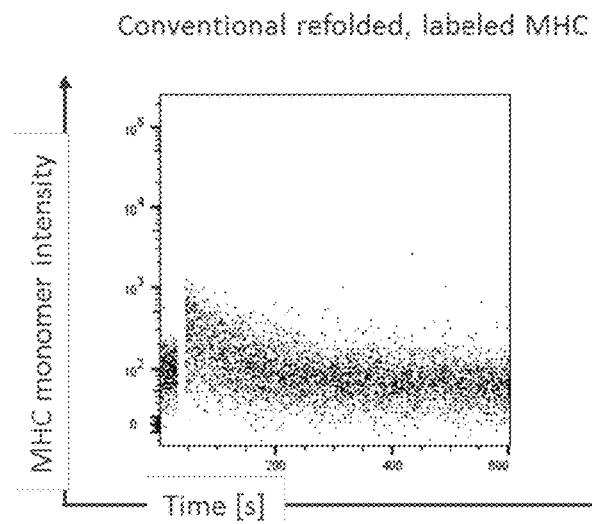
Figure 8B
UV-peptide exchanged, labeled MHC
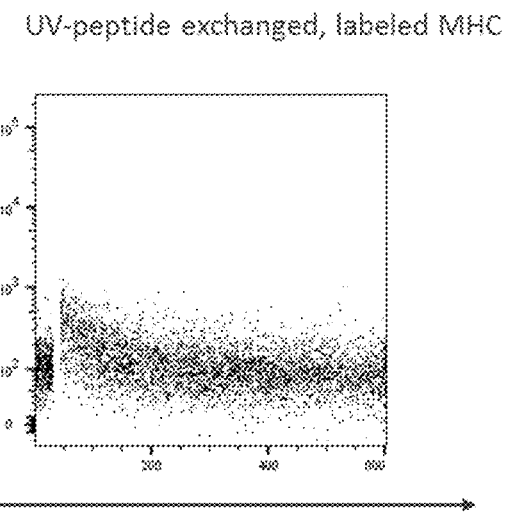
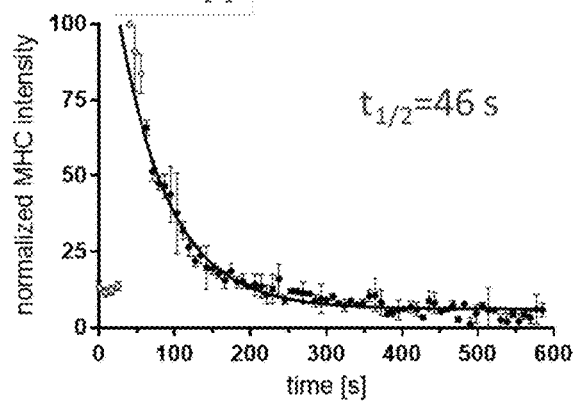
Figure 8C
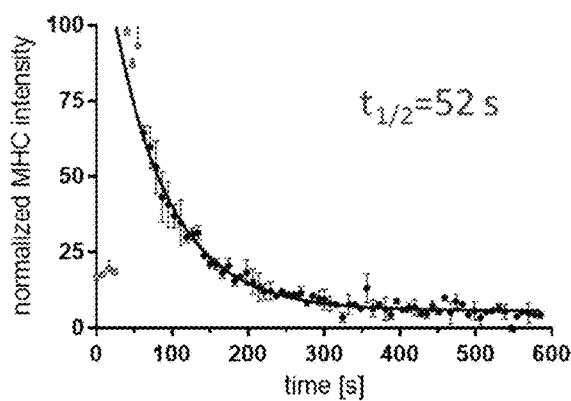
Figure 8D

Figure 10A
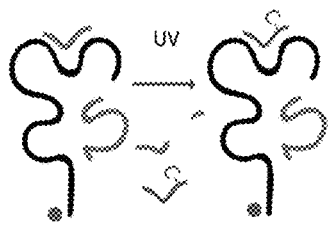
Figure 10B
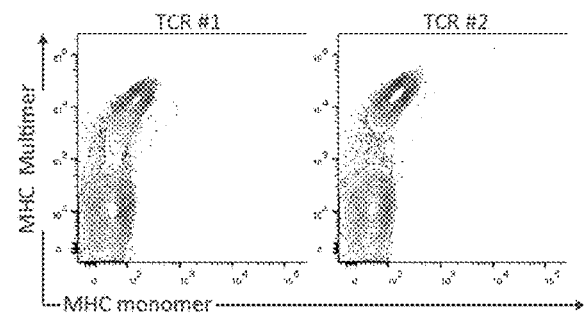
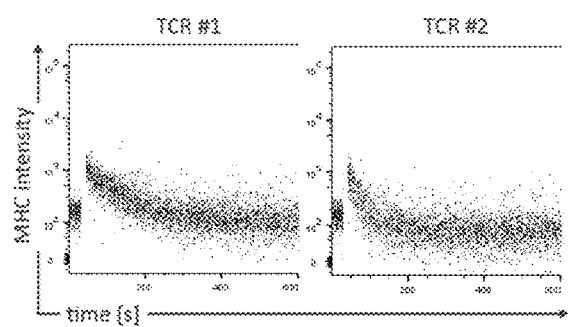
Figure 10C
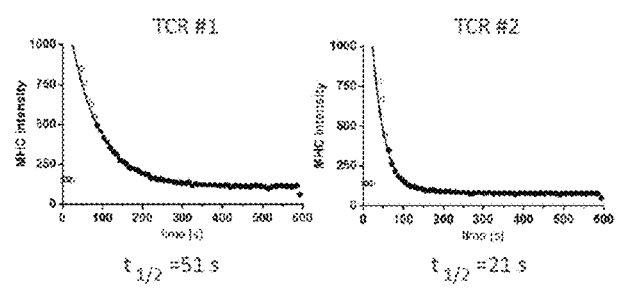
Figure 10D

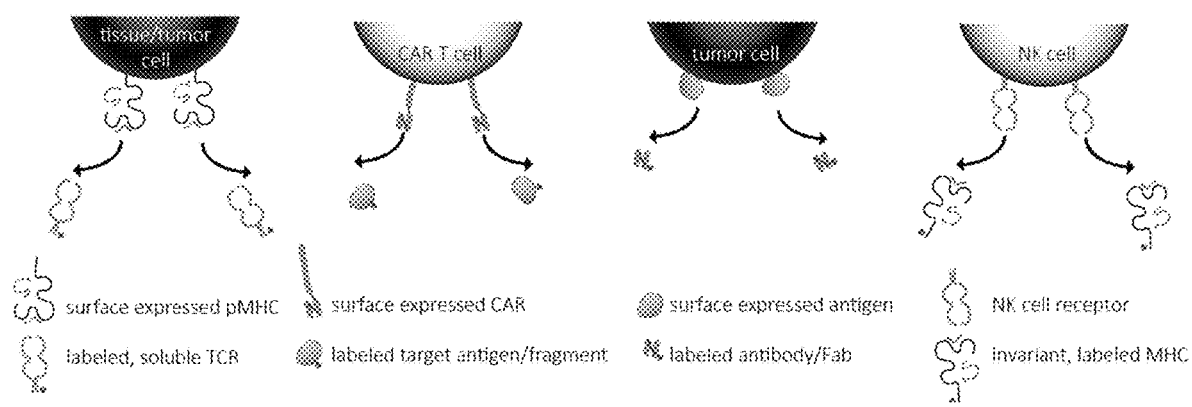
Figure 11A  Figure 11B  Figure 11C  Figure 11D

Figure 13A
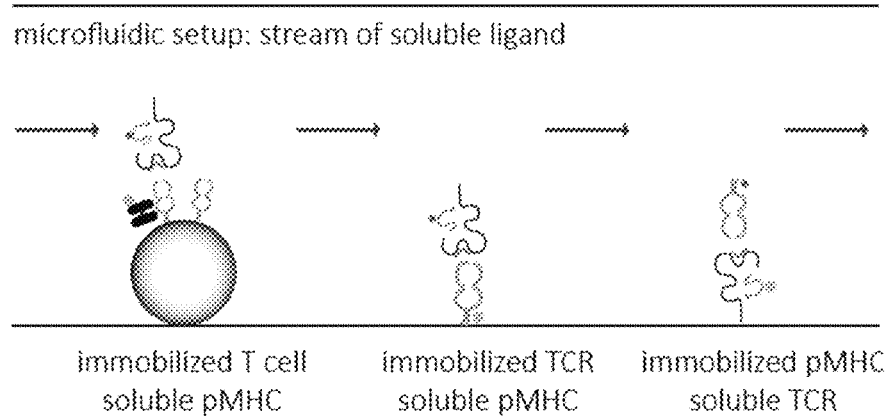
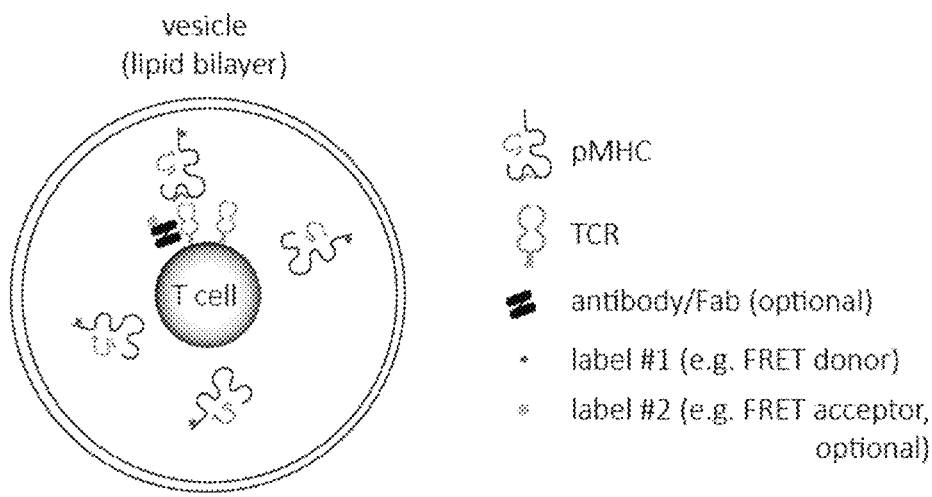
Figure 13B

Figure 16A
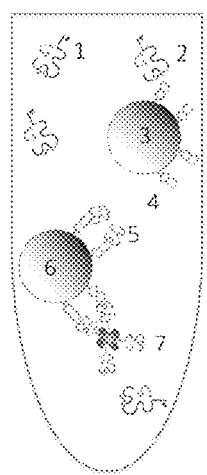
Figure 16B
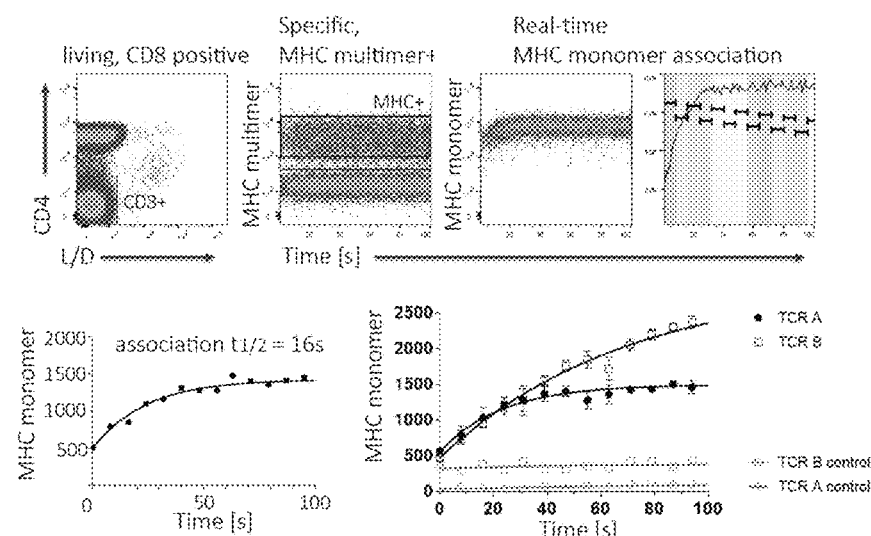
Figure 16C
Figure 16D

SEQUENCE LISTING

```
<160> NUMBER OF SEQ ID NOS: 2

<210> SEQ ID NO 1
<211> LENGTH: 9
<212> TYPE: PRT
<213> ORGANISM: Homo sapiens

<400> SEQUENCE: 1

Ser Leu Leu Met Trp Ile Thr Gln Cys
1               5

<210> SEQ ID NO 2
<211> LENGTH: 9
<212> TYPE: PRT
<213> ORGANISM: Homo sapiens

<400> SEQUENCE: 2

Ser Leu Leu Met Trp Ile Thr Gln Ala
1               5
```

METHODS OF MAKING AND USING SOLUBLE MHC MOLECULES

CROSS REFERENCE TO RELATED APPLICATIONS

This application claims priority to U.S. Provisional Patent Application Serial No. 62/373,695 filed on Aug. 11, 2016; the entirety of each of which is hereby incorporated by reference.

SEQUENCE LISTING

The instant application contains a Sequence Listing which has been submitted electronically in ASCII format and is hereby incorporated by reference in its entirety. Said ASCII copy, created on Aug. 11, 2017, is named K-1035_02_SL.txt and is 538 bytes in size.

FIELD OF THE INVENTION

This disclosure relates to soluble MHC molecules and methods for preparing such MHC molecules, which can be associated with a peptide of interest such as a cleavable peptide; uses for such molecules, including identifying T cell receptors and T cells expressing such T cell receptors are also provided.

BACKGROUND

MHC molecules are highly polymorphic proteins that regulate T cell responses (see, e.g., Owen et al., $7^{th}$ ed. W. H. Freeman, 2012). The MHC molecules that display peptide antigens in humans are known as human leukocyte antigen ("HLA"). HLA class I molecules can be divided into several families or "supertypes" based upon their ability to bind similar repertoires of peptides. HLA supertypes include A2, A3, and B7. For a peptide to be recognized by a T cell receptor (TCR) and thus activate cytotoxic T lymphocytes (CTLs) and induce effector functions such as lysis of a target cell, e.g., a tumor cell, it must be associated with, or "presented by," a major histocompatibility complex (MHC). MHCs exist in two classes, Class 1 MHC and Class 2 MHC. Class 1 MHCs comprise a polymorphic alpha chain (also referred to as a heavy chain) and a non-polymorphic beta microglobulin chain (also referred to as a light chain). The two chains are non-covalently associated with one another. Class 2 MHCs comprise an alpha and a beta chain, which associate with one another. Both classes of MHCs present peptide to TCRs. Thus, in order to identify peptides that are recognized by a given TCR it is necessary that the peptide is associated with a MHC molecule.

It can be beneficial to identify T cell receptors (TCRs) that specifically recognize peptide antigens of interest, in the context of MHCs. Such peptides can be derived from proteins expressed on infected (e.g., HPV) or cancerous cells and, thus, the ability to identify T cells that bind such peptides can lead to uses in adoptive cell therapy. However, it has proved to be challenging to identify the best T cell candidates for a given peptide antigen.

With the goal of identifying TCRs that bind to a peptide antigen of interest, various methods have been developed to screen TCR libraries, which can comprise T cells with different specificities or TCRs that are not associated with cells, for TCRs that recognize a given test peptide. These methods are either based on functional readouts analyzing T cells responding to stimulation with target cells (Vigano et al., (2012) Clin Dev Immunol 2012:153863), measuring binding kinetics of isolated, recombinant expressed TCRs associated with MHC monomer ligands in solution (Khilko et al., (1995) J Immunol Methods 183(1): 77-94; Bridgeman et al., (2012) Immunology 135(1): 9-18) or rely on recombinant expressed peptide loaded MHC multimers (Campanelli et al., (2002) Int Immunol 14(1): 39-44; Wang and Altman, (2003) J Immunol Methods 280(1-2): 25-35; Stone et al., (2011) J Immunol 187(12): 6281-6290). In other assays, both the TCR, as well as the MHC ligand are immobilized at exposing sites reducing the three-dimensional to a two-dimensional agitation to mimic a physiological cell-cell interaction (Huang et al., (2010) Nature 464(7290):932-936; Huppa et al., (2010) Nature 463(7283): 963-967; Puech et al., (2011) PLoS One 6(7):e22344).

Measurements based on reversible MHC multimers allow a simple and reproducible quantification of the TCR ligand $K_{off}$-rate as a major parameter for the quality of the TCR and T cell functionality on living cells (Nauerth et al., (2013) Science Translational Medicine 5(192):1-10; Hebeisen et al., (2015) Cancer Res 75(10):1983-91). For example, Nauerth et al. describe a method in which the dissociation of peptide-major histocompatibility complex (pMHC) molecules bound to surface-expressed TCRs can be monitored by real-time microscopy, which allows the calculation of a $k_{off}$ rate. See, e.g., Nauerth et al., (2013) Science Translational Medicine 5(192):1-10; Weissbrich et al., (2013) OncoImmunology 2(10):e26199. TCRs with desired characteristics can be selected and extracted by single cell PCR or TCR gene capture methods described in, e.g., Dossinger et al., (2013) PLoS One 8:e61384; Linnemann et al., (2013) Nat Med 19(11):1534-1541; Hamana et al., (2016) Biochem Biophys Res Commun 474(4):709-714; and Zhang et al., (2016) Sci Transl Med 8(341):341ra377.

A challenge for these methods, notably those described in Huppa et al., (2010) Nature 463(7283):963-967, Hebeisen et al. (2015) Cancer Res 75(10):1983-91) and Nauerth et al., (2013) Science Translational Medicine 5(192): 1-10, is the fact that many are not compatible with high throughput operations due to the elaborate generation of the labeled MHC monomer ligands. The methods are limited to previously defined peptide specificities, not allowing screening of peptide libraries derived from novel and diverse target antigens such as patient specific neo-peptides. Another challenge these methods face is that, importantly, they are not able to query a T cell/TCR library with peptides that comprise a cysteine residue (hereinafter a "cysteine peptide") for binding to a TCR. The inability to screen using test peptides that comprise a cysteine residue, which is not compatible with the chemistries of labeling processes based on attachment via sulfhydryls, effectively removes this entire class of peptide antigen from the scope of current screening activities and assays. The instant disclosure solves these and other problems.

SUMMARY

In one aspect, a method of generating a detectably-labeled, soluble MHC monomer loaded with a cleavable peptide is provided. In one embodiment, the method comprises (a) forming a labeling mixture comprising: (1) TCEP; (2) a maleimide-conjugated detectable label; and (3) a soluble MHC comprising an alpha chain and a beta chain, further comprising a non-naturally occurring cysteine residue, wherein the MHC is loaded with a cleavable peptide; (b) incubating the labeling mixture at a desired incubation temperature a desired incubation period; and (c) removing unbound maleimide-conjugated detectable label from the labeling mixture. In various embodiments the label is selected from the group consisting of a radiolabel, fluorescent agents, chromogenic agents, chemiluminescent agents and magnetic particles, and in a specific embodiment the label is a fluorescent dye and can be selected from the group consisting of an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellowl, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. In a further embodiment, the incubation period is about 2.5 hours or less and the incubation temperature is about 20-24° C., and in another embodiment the incubation period is about 12 hours and the incubation temperature is about 4° C. Moreover, in additional embodiments the MHC is a MHC I. In yet other embodiments, the non-naturally occurring cysteine is introduced at one or both of (a) position 67 or 88 of the MHC I beta chain; and (b) the C-terminus of the MHC I alpha chain. In other embodiments the MHC complex is a MHC II. And in still further embodiments, the non-naturally occurring cysteine is introduced at one or both of (a) the C-terminus of the MHC II beta chain; and (b) the C-terminus of the MHC II alpha chain. In some embodiments the cleavable peptide is cleavable by UV light. A detectably-labeled, soluble MHC monomer produced by the method is also provided.

In another aspect, a method of identifying a TCR that associates with a MHC-peptide complex is provided. In one embodiment, the method comprises (a) providing a multimer complex comprising a backbone reversibly associated with a plurality of detectably-labeled, soluble MHC monomers, each loaded with a peptide of interest; (b) contacting the multimer complex with a TCR under conditions that allow the formation of a MHC-peptide-TCR complex; (c) disrupting the multimer complexes; and (d) determining the MHC-peptide-TCR $K_{off}$, wherein the $K_{off}$ indicates a degree to which a TCR associates with the MHC-peptide complex.

In some embodiments, the method further comprises first forming the multimer complex by providing a detectably-labeled, soluble MHC monomer loaded with a cleavable peptide described herein; exchanging the cleavable peptide with the peptide of interest, thereby generating a detectably-labeled, soluble MHC monomer loaded with the peptide of interest; and forming the multimer complex by reversibly associating the backbone with a plurality of the detectably-labeled, soluble MHC monomers, each loaded with the peptide of interest.

In one embodiment peptide of interest comprises a cysteine residue. In other embodiments a $K_{off}$ of about 20 seconds or longer indicates that the TCR associates with the MHC-peptide complex and in other embodiments a $K_{off}$ of about 15 to about 500 seconds or longer indicates that the TCR associates with the MHC-peptide complex. In still other embodiments, the TCR library comprises a plurality of T cells, each T cell presenting a complete TCR, and one or both of a CD4 molecule and a CD8 molecule. In other embodiments, the method further comprising transducing a T cell with a nucleic acid encoding the alpha and beta chains of the TCR. In some embodiments, the method is performed at a temperature of between about 4° C. and about 37° C., and in other embodiments the temperature is about 20° C. In one embodiment, the peptide of interest comprises a neo antigen. In yet another embodiment, the method further comprises isolating the TCR genes from the T cell selected based on kinetic properties described herein (e.g., $K_{on}$, $K_{off}$, etc.).

In another aspect, a method of selecting a T cell suitable for adoptive transfer is provided. In one embodiment the method comprises (a) providing a multimer complex comprising a backbone reversibly associated with a plurality of a detectably-labeled, soluble MHC monomer loaded with a peptide of interest; (b) contacting the multimer complex with a TCR library comprising a plurality of T cells expressing a plurality of TCRs under conditions that allow the formation of a MHC-peptide-TCR complex; (c) disrupting the multimer complexes; (d) determining $K_{off}$ of a MHC-peptide-TCR complex; and (e) selecting a T cell for adoptive therapy, wherein the T cell expresses a TCR having a $K_{off}$ for the MHC-peptide complex of about 15 seconds to about 500 seconds.

In some embodiments, wherein the method further comprises first forming the multimer complex by providing a detectably-labeled, soluble MHC monomer loaded with a cleavable peptide described herein; exchanging the cleavable peptide with the peptide of interest, thereby generating a detectably-labeled, soluble MHC monomer loaded with the peptide of interest; and forming the multimer complex by reversibly associating the backbone with a plurality of the detectably-labeled, soluble MHC monomer loaded with the peptide of interest.

In various embodiments, the TCR library comprises a plurality of T cells, each T cell presenting a complete TCR, and one of a CD4 molecule and a CD8 molecule. In some embodiments, the method further comprises (h) expanding the T cell selected in (g) to a population of at least about $1 \times 10^2$ T cells; and (i) administering a desired number of T cells to a subject. In some embodiments at least about $1 \times 10^6$ T cells are administered to the subject. In some embodiments, at least about $1 \times 10^6$ T cells/kg bodyweight, about $1 \times 10^7$ T cells/kg, about $1 \times 10^8$ T cells/kg bodyweight, or about $1 \times 10^9$ T cells/kg bodyweight are administered to the subject.

In still another aspect, a method of identifying member of a binding pair of interest is provided. In one embodiment, the method comprises (a) forming a labeling mixture comprising: (1) TCEP; (2) a maleimide-conjugated detectable label; and (3) a first member of a binding pair; (b) incubating the labeling mixture at a desired incubation temperature a desired incubation period; (c) removing unbound maleimide-conjugated detectable label from the labeling mixture; (d) contacting the one member of a binding pair with a screening library comprising a known or suspected second member of the binding pair under conditions that allow the formation of an association complex; and (e) detecting the formation of an association complex. In various embodiments, the label is selected from the group consisting of a radiolabel, fluorescent agents, chromogenic agents, chemiluminescent agents and magnetic particles, and in one embodiment, the label is a fluorescent dye. In various embodiments, the fluorescent dye is selected from the group consisting of an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. In other embodiments, the first binding partner comprises a cysteine residue, and in other embodiments the binding pair is selected from the group consisting of a (i) an antigen binding molecule comprising a Fab fragment and a protein expressed on the surface of a tumor cell, (ii) a scFv and a protein expressed on the surface of a tumor cell, (iii) a DNA binding protein and DNA, (iv) a recombinant protein and a chimeric antigen receptor, and (v) a transmembrane adhesion molecule and its cognate ligand. In a specific embodiment, the binding pair is a recombinant protein and the cell surface receptor is a chimeric antigen receptor. In other embodiments, the screening library comprises a plurality of T cells, each T cell presenting a complete TCR, and one or both of a CD4 molecule and a CD8 molecule. In yet further embodiments, the method is performed at a temperature of between about 4° C. and about 37° C. In still a further embodiment, the method further comprises the step of determining a kinetic property of an association complex comprising the first and second members of the binding pair, the kinetic property selected from the group consisting of a $K_{off}$ and $K_{on}$, wherein the kinetic property indicates a degree to which a ligand associates with an association complex. In some embodiments, a $K_{off}$ of about 15 seconds or longer indicates that the binding partners form an association complex and in other embodiments, a $K_{off}$ of about 15 to about 500 seconds or longer indicates that the binding partners form an association complex.

In one aspect, the present invention provides a method of identifying a TCR that associates with a MHC-peptide complex, the method comprising: (a) contacting cells expressing one or more TCRs with a plurality of detectably-labeled multimer complexes, each comprising a backbone irreversibly associated with a plurality of MHC monomers loaded with a peptide of interest, wherein cells associated with the multimer complexes (multimer positive cells) express a TCR that is specific to a MHC monomer loaded with the peptide of interest and cells not associated with the multimer complexes (multimer negative cells) do not express a TCR that is specific to a MHC monomer loaded with the peptide of interest; (b) introducing a plurality of distinctively-labeled, soluble MHC monomers, each loaded with the peptide of interest, under conditions allowing formation of a MHC monomer-peptide-TCR complex; (c) detecting the formation of specific MHC monomer-peptide-TCR complexes by subtracting signals of the MHC monomers associated with the multimer negative cells from total signals of the MHC monomers; (d) determining the rate of formation of the specific MHC monomer-peptide-TCR complexes detected in step (c) as a function of time, thereby determining the MHC monomer-peptide-TCR $K_{on}$, wherein the $K_{on}$ indicates a degree to which a TCR associates with the MHC monomer-peptide complex.

In some embodiments, the detectably-labeled multimer complexes are formed by multimerizing biotinylated MHC monomers loaded with the peptide of interest on Streptavidin, wherein biotin or Streptavidin is detectably labeled.

In some embodiments, wherein the method further comprises first providing a distinctively-labeled, soluble MHC monomer loaded with a cleavable peptide as described herein; and exchanging the cleavable peptide with the peptide of interest, thereby generating a distinctively-labeled, soluble MHC monomer loaded with the peptide of interest.

In some embodiments, the distinctively-labeled, soluble MHC monomer loaded with the peptide of interest is maintained at a constant concentration. In some embodiments, the constant concentration of the distinctively-labeled, soluble MHC monomers ranges from 10-50 μM.

In some embodiments, a $K_{on}$ of about 50 seconds or less indicates a desired degree to which the TCR associates with the MHC monomer-peptide complex. In some embodiments, a $K_{on}$ of about 10 to about 30 seconds indicates a desired degree to which the TCR associates with the MHC monomer-peptide complex.

In some embodiments, the TCR is provided in a library comprising a plurality of T cells, each T cell presenting a complete TCR, and one or both of a CD4 molecule and a CD8 molecule.

In some embodiments, the methods of the present invention further comprise a step of transducing a T cell with a nucleic acid encoding the alpha and beta chains of the TCR.

In some embodiments, the formation of the MHC monomer-peptide-TCR complex is detected by flow cytometry.

In some embodiments, the method is performed at a temperature of between about 4° C. and about 37° C. In some embodiments, the method is performed at a temperature between about 20-25° C. In some embodiments, the method further comprises a step of labeling the cells with an anti-CD4 and/or anti-CD8 antibody.

In some embodiments, the peptide of interest comprises a neo antigen.

In some embodiments, the present invention provides a method of determining the dissociation constant ($K_D$) between a TCR and a MHC-peptide complex, comprising: (a) determining $K_{off}$ between the TCR and the MHC-peptide complex according to the methods of described herein; (b) determining $K_{on}$ between the TCR and the MHC-peptide complex according to the methods described herein; (c) calculating the dissociation constant ($K_D$) by dividing the $K_{off}$ determined at step (a) by the $K_{on}$ determined at step (b). In some embodiments, the $K_{off}$ and $K_{on}$ are determined using T cells expressing the TCR and a co-receptor, wherein the calculated $K_D$ indicates the dissociation constant of the binding between the TCR with the co-receptor and MHC-peptide complex. In some embodiments, the co-receptor is a CD4 or CD8 receptor. In some embodiments, the method further comprises a step of determining an association constant ($K_A$) based on the $K_D$ calculated.

BRIEF DESCRIPTION OF THE FIGURES

FIG. 3A shows a complex comprising a TCR expressed on the surface of a T cell binding to a pMHC complex which is multimerized on a Strep-Tactin® while FIG. 3B shows the release of the Strep-Tactin through the action of biotin, and FIG. 3C shows the TCR avidity-mediated release of pMHC from the TCRs.

FIGS. 4A to 4D are a series of cartoons and plots demonstrating the observation that MHC monomers loaded with cysteine peptides and labeled using previously known methods disrupt the staining of T cells expressing TCRs; FIG. 4A depicts the non-specific labeling of a cysteine peptide that can occur, while FIG. 4B depicts how the non-specific binding can prevent interaction between pMHC and TCRs, and FIGS. 4C and 4D demonstrate quantitatively how T cell staining can be disrupted by non-specific labeling.

FIGS. 7A to 7E are a series of cartoons and plots depicting a two-dye labeling process as disclosed herein.

FIGS. 8A to 8D are a series of plots demonstrating that pMHC monomers labeled as described herein are functional for TCR ligand $k_{off}$-rate measurement.

FIGS. 10A to 10D are a cartoon and 6 lots demonstrating that the disclosed labeling methods allow the analysis of TCRs specific for cysteine-containing peptides in a TCR ligand $k_{off}$ rate assay.

FIGS. 11A to 11D are a series of four cartoons depicting potential cell surface receptor-ligand interactions using detectably labeled, soluble ligands generated using the disclosed methods; FIG. 11A shows a detectably labeled, recombinantly expressed TCR for analyzing pMHC expression on target cells, such as tumor cells or healthy tissue cells, and FIG. 11B shows the use of detectably labeled, recombinantly expressed antigenic target proteins or fragments thereof for measuring chimeric antigen receptor binding strength, while FIG. 11C shows the use of detectably labeled, scFv fragments for measuring their binding strength to the surface expressed target protein, and finally FIG. 11D shows the use of detectably labeled, invariant MHC monomers for identification of NK cells.

FIG. 12A shows the pMHC immobilized either irreversibly or reversibly on a surface such as a planar lipid bilayer, and in the figure movement of labeled MHC monomers is restricted lateral, and FIG. 12B shows the pMHC monomers immobilized on an opposing target such as a red blood cell or a bead.

FIGS. 13A and 13B are a series of two cartoons depicting experimental setups to analyze the monomeric interaction between a TCR and a pMHC without previous multimerization of the pMHC to allow binding to specific T cells; FIG. 13A shows the T cell, a recombinant TCR or a recombinant pMHC immobilized on a microfluidic device, and FIG. 13B shows the T cell expressing the TCR captured in a lipid bilayer vesicle in the presence of soluble pMHC ligands labeled with the methods described herein.

FIG. 16A illustrates a cell suspension comprising a mixture of TCR transduced T cells. Specific surface expressed TCRs of interest are labelled with a MHC multimer complex conjugated to a fluorescent label. Unspecific T cells lack the MHC multimer label. Soluble, MHC monomers labeled with the disclosed method are added into the cell suspension. 1-soluble, labelled pMHC; 2-unspecificly bound, labelled pMHC; 3-unspecific T cell; 4-surface expressed TCR; 5 specifically bound, labelled pMHC; 6-specific T cell stained with 7-detectable pMHC multimer. FIG. 16B is a series of plots showing the gating strategy and monitoring of pMHC monomer association to the specific T cells. FIG. 16C is a plot with the corrected fluorescence values of the pMHC monomer association. FIG. 16D compares the association times for two TCRs specific for the identical peptide-MHC monomer.

DETAILED DESCRIPTION

Figure 1:
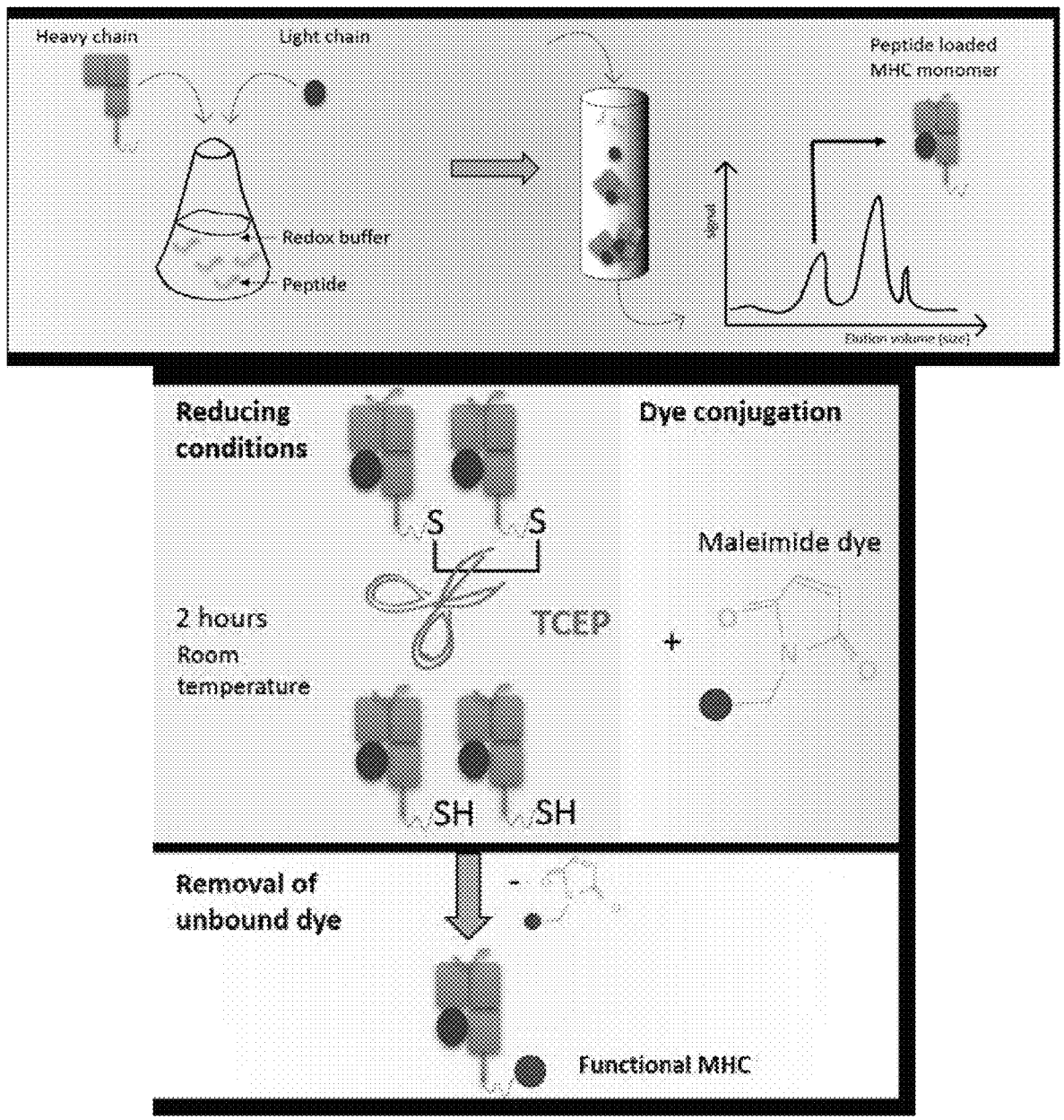
FIG. 1 is a diagram graphically depicting the steps of one embodiment of the disclosed methods.
Figure 2:
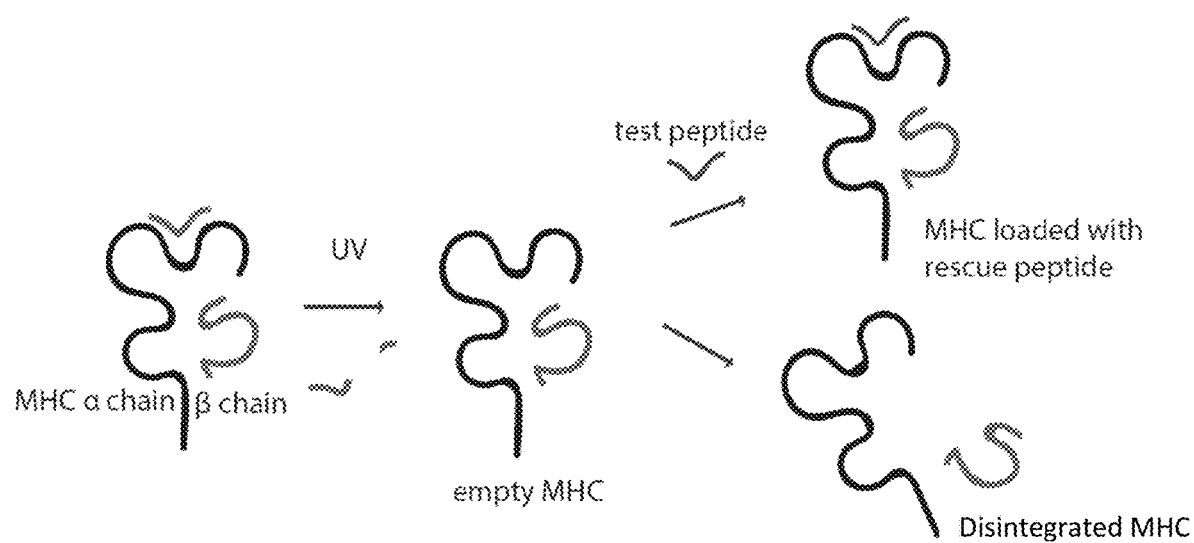
FIG. 2 is a cartoon depicting the general steps and strategy of a UV-peptide exchange for high throughput generation of MHC monomers with different specificities.

The instant disclosure provides an improved TCR ligand $K_{off}$-rate assay to enable a broader application through a novel combination, which can be readily adapted to leverage current peptide exchange methods (see, e.g., Nauerth et al., (2013) *Science Translational Medicine* 5(192):1-10; Rodenko et al., (2006) *Nat Protoc* 1(3):1120-1132; Gannon et al., (2015) *J Immunol* 195(1):356-366; Hebeisen et al., (2015) *Cancer Res* 75(10):1983-1991; U.S. Pat. No. 7,776, 562). The disclosed methods enable pMHC monomer preparation in a high-throughput manner that was previously not feasible, thus enabling the rapid screening of TCR candidates for pMHC binding. Further, the disclosed methods allow the analysis of TCR candidates recognizing specific pMHC complexes wherein the peptide comprises the amino acid cysteine; this class of peptide could not be studied using previously known methods, due to the fact that the presence of the cysteine residue can interfere with or even abolish the ability to determine an accurate $k_{off}$-rate measurement, thus preventing the study of an entire class of peptides that comprises potentially interesting candidates for TCR binding.

The labeling procedure for MHC monomers described herein can be combined with peptide exchange technology and methods. Using the disclosed methods, labeled MHC monomers can be produced in a high throughput manner, and can be loaded with cysteine containing peptides, (which previously interfered with known assays), thus facilitating the analysis of a broader spectrum of specific T cells.

As noted herein, previous studies demonstrate that many TCRs specific for cysteine peptides cannot be analyzed for their structural TCR binding avidity in the TCR ligand $k_{off}$-rate assay using previously available methods, including those that comprise the labeling of soluble MHCs. Previously-described labeling procedures can undesirably modify cysteine residues in the peptide, and therefore interfere with the interaction to the specific TCR, expressed on a T cell, and inhibit staining (see FIG. 4).

Cysteine peptide-specific TCRs are relevant for immunotherapy. The HLA-A*02:01 NY-ESO-1$_{157-165}$ specific, affinity enhanced TCR 1G4, for example, recognizes the peptide SLLMWITQC (SEQ ID NO:1) and shows encouraging clinical responses in metastatic synovial sarcoma, melanoma and multiple myeloma (Robbins et al., (2015) Clin Cancer Res 21(5): 1019-27; Rapoport et al., (2015) Nat Med 21(8):914-2). One strategy to analyze these TCRs is the exchange/mutation of cysteine residues in the peptide with other amino acids. For example, multiple cysteine residues have been replaced with the isosteric amino acid to generate MHC multimers (Schepers et al., (2002) J Immunol 169(6): 3191-9). TCRs specific for the NY-ESO-1$_{157-165}$ SLLMWITQC (SEQ ID NO: 1) peptide have been analyzed for TCR binding avidity using the peptide analogue SLLMWITQA (SEQ ID NO:2) (Hebeisen et al., Cancer Res 75(10):1983-91).

Although the MHC multimers allow binding to the specific TCRs, the binding kinetics, as well as functional response towards the modified peptide can be altered (Chen et al., (2005) J Exp Med 201(8): 1243-55; Romero et al., (2001) Clin Cancer Res 7(3 Suppl):766s-772s; Wang et al., (2002) J Immunol 169(6):3137-45; Aleksic et al., (2010) Immunity 32(2):163-74). The binding affinity of an individual TCRs to a modified peptide MHC may be affected differently as compared to other TCRs specific for the identical peptide. Further, the comparison of the kinetics to TCRs specific for other non-cysteine and non-modified peptides is limited.

An approach circumventing the outlined limitations of previously disclosed methods of studying cysteine peptides and MHCs loaded with cysteine peptides is disclosed herein. The loading of a cysteine peptide following the labeling procedure of the MHC monomer by UV peptide exchange prevents any modification of the cysteine; functional MHC monomers for TCR ligand $k_{off}$-rate measurement were generated and are presented in the Examples that follow. Thus, the instant disclosure provides a modified labeling procedure based, in one aspect, on the replacement of the reducing agent dithiothreitol (DTT) with tris(2-carboxyethyl)phosphin (TCEP). These compounds are agents that are added in order to reduce the non-natural occurring cysteine residue on the MHC monomer for the covalent conjugation to the maleimide dye of the disclosed methods.

Figure 9:
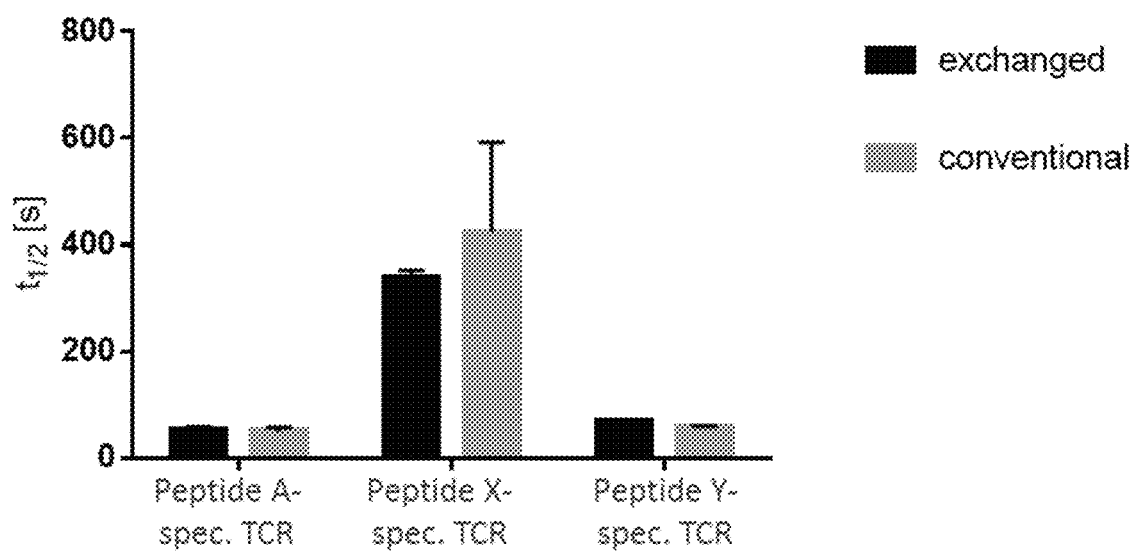
FIG. 9 is a bar graph demonstrating that the dissociation of pMHC monomers, which were labeled using the methods provided herein, from TCRs compares to standard MHC monomers.

Previously known labeling procedures are based on long pretreatment with DTT and buffer exchanges and allowed the labeling of MHC monomers refolded in the presence of the test peptide (Nauerth et al., (2013) Sci Transl Med 5(192):192ra87). DTT pretreatment and maleimide labeling of MHC monomers loaded with a UV-labile peptide, which is used for biotinylated, unlabeled MHC monomers in a previous method (Rodenko et al., (2006) Nat Protoc 1(3): 1120-32), resulted in non-functional MHC monomers (Weissbrich, (2015) "T cell Receptor Binding Avidity of Antigen-specific CD8+ Cytotoxic T cells in Chronic Infection," PhD Dissertation, Technical University of Munich). Surprisingly, replacing DTT with TCEP and using it without pretreatment in combination with the reactive maleimide label, it was possible to generate functional UV-peptide exchange MHC monomers. Upon peptide exchange with a test cysteine peptide of interest, the staining and the dissociation was comparable to MHC monomers prepared with the previous methods (see FIGS. 7, 8 and 9). Loading the cysteine peptide on the labeled MHC monomers by UV-peptide exchange and multimerizing those on Strep-Tactin® allowed to stain specific T cells and determine the MHC monomer dissociation rate (FIG. 10).

The methods provided herein, which are broadly directed to the labeling of UV-peptide exchange MHC monomers, therefore broaden the range of applications for the TCR ligand $k_{off}$-rate assay. Notably, cysteine peptide-specific TCRs can now be analyzed without modification of the peptide, opening the study of a class of peptides that was limited by the previous methods. Further, the high throughput generation of labeled MHC monomers with different peptides reduces cost and time. The amount of a specific test peptide needed for the disclosed methods is more than 12-fold reduced. Small scale peptide libraries can now be synthesized and used for screening of TCR libraries using the disclosed methods. In this way, novel, previously undescribed peptides, such as patient-specific neo-epitopes, can be tested and/or selected TCRs can be queried against variants of the wildtype peptide to identify cross-reactive peptide variants, e.g., to identify off-target toxicity or to analyze virally mutated escape variants.

Thus, the disclosed methods broaden the ability to identify TCRs that bind specific pMHC complexes. For example, using the disclosed methods cysteine-peptide specific TCR candidates can be studied, which was not previously possible; peptide libraries including novel specificities can be rapidly queried by different TCRs; moreover, TCRs found to bind to pMHC complexes can be studied using peptide mimotope libraries to determine whether the TCR cross-reacts with a peptide that is different from the peptide of a pMHC found to bind to the TCR, in a high-throughput manner.

I. Definitions

In order that the present disclosure may be more readily understood, certain terms are first defined. As used in this application, except as otherwise expressly provided herein, each of the following terms shall have the meaning set forth below. Additional definitions are set forth throughout the application.

Units, prefixes, and symbols are denoted herein in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

Unless defined otherwise, all technical and scientific terms used herein have the same meaning as commonly understood by one of ordinary skill in the art to which this disclosure is related. For example, *The Concise Dictionary of Biomedicine and Molecular Biology*, Juo, Pei-Show, 2$^{nd}$ ed., CRC Press (2002); *The Dictionary of Cell and Molecular Biology*, 3rd ed., Academic Press (1999); and *The Oxford Dictionary Of Biochemistry And Molecular Biology*, Revised, Oxford University Press (2000), provide those of skill in the art with a general dictionary for many of the terms used in this disclosure.

It is understood that wherever aspects are described herein with the language "comprising," otherwise analogous aspects described in terms of "consisting of" and/or "consisting essentially of" are also provided.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially" can mean within one or more than one standard deviation per the practice in the art. Alternatively, "about" or "comprising essentially" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

As used herein, the term "and/or" is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the term the use of the alternative (e.g., "or") should be understood to mean either one, both, or any combination thereof of the alternatives.

As used herein, the term the terms "a" and "an" are used per standard convention and mean one or more, unless context dictates otherwise.

As used herein, the term "binding avidity" means the strength of the sum total of non-covalent interactions between the binding sites of a molecule (e.g., an TCR) and its binding partner (e.g., an antigenic peptide loaded on a MHC). Unless indicated otherwise, as used herein, "binding avidity" refers to intrinsic binding affinity which reflects a 1:1:1 interaction between members of a ternary binding pair (e.g., the TCR in combination with CD8 co-receptor binding to a pMHC monomer) or a 1:1 interaction between members of a binary binding pair (e.g., the TCR expressed on CD8 negative cells and pMHC; a TCR and a pMHC with abolished CD8 binding; a CAR and an antigen). The structural binding avidity of a molecule X (combined with molecule Y) for its partner Z can generally be represented by the dissociation constant ($K_D$) or conversely the association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., a pMHC with a CD8 co-receptor and a TCR, and $k_{off}$ refers to the dissociation of, e.g., a pMHC from a TCR and the CD8 co-receptor.

As used herein, the term "cleavable peptide" means a peptide that is covalently or non-covalently associated with a MHC monomer, and which can be separated from the MHC monomer by breaking one or more non-naturally occurring amino acids in the cleavable peptide. In various embodiments, a cleavable peptide comprises a non-naturally occurring amino acid that facilitates the joining of the peptide to the MHC. Exemplary methods of cleaving a cleavable peptide from an MHC include UV light, chemical reagent-mediated and oxidative cleavage (Rodenko et al., (2006) *Nat Protoc* 1(3): 1120-1132, Rodenko et al., (2009) *J Am Chem Soc* 131(34): 12305-12313, Amore et al., (2013) *Chembiochem* 14(1): 123-131).

As used herein, the term "detectable label" means a chemical or biochemical moietie associated with, and used for, facilitating a determination of the presence of a molecule of interest, such as a MHC monomer. When a label is associated with a molecule of interest the molecule is referred to as detectably labeled. Thus, a detectably labeled MHC monomer means a MHC monomer with which a detectable label is associated. Examples of detectable labels include, but are not limited to, fluorescent agents, chromogenic agents, chemiluminescent agents, magnetic particles, and the like. Specific examples of each of these types of labels are provided herein.

As used herein, the term "isolated" means a molecule such as a peptide or nucleic acid, or derivative thereof, which is not in its natural milieu. No particular level of purification is required for a molecule to be isolated. For example, an isolated polypeptide such as a TCR or an MHC can simply be removed from its native or natural environment. Recombinantly produced polypeptides and proteins expressed in or on the surface of host cells are considered isolated for the purpose of the instant disclosure, as are native or recombinant polypeptides which have been separated, fractionated, or partially or substantially purified by any suitable technique.

As used herein, the term $K_{off}$ means the rate at which a binding complex dissociates to its component binding partners (which themselves can comprise a complex comprising two or more binding partners). By way of example, when used in the context of a pMHC-TCR interaction, $K_{off}$ means the rate at which a pMHC complex dissociates from a given TCR. The TCR can be recombinantly expressed and disposed on a surface, or it can be expressed on the surface of a cell, such as a cell expressing the co-receptor CD4 or CD8 that contributes to the pMHC-TCR dissociation and $k_{off}$-rate, and in this case $K_{off}$ refers to $K_{3D}$, since the binding complex comprises three members, the TCR, the pMHC and either CD4 or CD8. If CD4 or CD8 is not present, or is present but in a mutated form such that it cannot associate with the pMHC-TCR complex, $K_{off}$ simply represents the dissociation of the binary pMHC-TCR complex. Thus, unless stated otherwise the term $K_{off}$ represents the dissociation of binding complexes comprising two or more binding partners and reflects the number of binding partners in the complex.

As is the case with all the methods disclosed herein, in other embodiments the TCR and/or the pMHC can be disposed in a non-naturally occurring environment, such as a bilayer, associated with a surface such as a welled plate, or on a cell that does not normally express a TCR and/or MHC. It can be calculated by recording a detection signal (e.g., a fluorescent signal) decay of a labeled pMHC from a TCR as a function of time. The half-life time ($t_{1/2}$) of a pMHC-TCR interaction can be calculated from the $k_{off}$-rate ($=\ln2/k_{off}$). Half-life times reported herein, e.g., in the Examples, were all calculated using this relationship. See, e.g., Nauerth et al., (2013) *Sci. Trans. Med.* 5(192):1-10).

As used herein, the term $K_{on}$, means the rate at which a binding complex associates with its component binding partners (which themselves can comprise a complex comprising two or more binding partners). As an example, when used in the context of a pMHC-TCR interaction, $K_{on}$ means the rate at which a pMHC complex associates to a given TCR. It can be calculated by recording signal increase of a labeled pMHC as it associates with a TCR as a function of time. Again, in other embodiments the TCR and/or the MHC can be disposed in a non-naturally occurring environment, such as a bilayer, associated with a surface such as a welled plate, or on a cell that does not normally express a TCR and/or a MHC.

The binding complex kinetic properties $K_{off}$ and $K_{on}$ inform the kinetic property $K_D$. $K_D$ can be calculated based on the observed values of $K_{off}$ and $K_{on}$. As used herein, $K_D$ is defined as the ratio of $K_{off}$ to $K_{on}$ ($K_D = K_{off}/K_{on}$).

As used herein, the term "MHC monomer" means a protein complex comprising two non-covalently associated chains, an alpha chain and a beta chain, encoded by a cluster of genes that plays a role in control of the cellular interactions responsible for physiologic immune responses. In humans, the MHC complex is also known as the human leukocyte antigen (HLA) complex. See, e.g., Owen et al., *Kuby Immunology* 7th ed. W. H. Freeman, 2012, Murphy et al., (2016) *Janeway's Immunobiology*, 9th ed., Garland Science, incorporated herein in its entirety for any purpose. The term "MHC monomer" encompasses both class I MHCs (comprising a heavy (alpha) chain and a light (beta or beta microglobulin) chain and class II MHC (comprising alpha and beta chains) complexes.

As used herein, the terms "protein" and "polypeptide" are used interchangeably and mean a chain of two or more amino acids or amino acid analogs (including non-naturally occurring amino acids), with adjacent amino acids joined by peptide (—NHCO—) bonds.

As used herein, the term "reducing agent" means an element or compound that donates an electron to a different element or compound under conditions suitable for the electron to be donated by the reducing agent and received by the receiving element or compound.

As used herein, the term "residue" refers to an amino acid residue, mimetic or analog that incorporated into a peptide or protein by an amide bond or amide bond mimetic. The term "amino acid," as used herein, refers to the twenty conventional (e.g., naturally occurring) amino acids and their abbreviations follow conventional usage. See, e.g., *Immunology: A Synthesis*, 2nd ed., Golub and Green (eds.), Sinauer Assoc., (1991), which is incorporated herein by reference for any purpose.

Stereoisomers (e.g., D-amino acids) of the twenty conventional amino acids, unnatural amino acids such as alpha-, alpha-disubstituted amino acids, N-alkyl amino acids, lactic acid, norleucine and other unconventional and non-naturally occurring amino acids can also be suitable components for polypeptides of the disclosed compounds and methods. Examples of unconventional amino acids include: gamma-carboxyglutamate, epsilon-N,N,N-trimethyllysine, e-N-acetyllysine, O-phosphoserine, N-acetylserine, N-formyl-methionine, 3-methylhistidine, 5-hydroxylysine, sigma-N-methylarginine, homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid, thioproline and similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As used herein, the term "subject" is used interchangeably with the term "patient" and means any human who is being treated for an abnormal physiological condition, such as cancer, or has been formally diagnosed with a disorder, those without formally recognized disorders, those receiving medical attention, those at risk of developing the disorders, etc. The terms "subject" and "patient" include human and non-human animal subjects.

As used herein the terms "T cells" or "T lymphocytes" are used interchangeably and mean the subset of lymphocytes originating in the thymus (or ex vivo artificial thymus organ-like systems) and having heterodimeric receptors that normally associate with one or more proteins of the CD3 complex (e.g., a rearranged T cell receptor, the heterodimeric protein on the T cell surfaces responsible for antigen/MHC specificity of the cells).

Additional definitions can be found in the disclosure herein below.

II. Exemplary Embodiments

Current methodologies allow large libraries of peptides to be loaded on their respective MHC monomers, thereby creating diverse sets of peptide loaded MHC monomers which can be used to isolate, identify and characterize T cells from various source materials that express TCRs that specifically recognize a given peptide antigen. See, e.g., Rodenko et al., (2006) *Nature Protocols* 1(3):1120-32; Hadrup & Schumacher (2010); *Cancer Immunol Immunother* 59(9):1425-1433; Hombrink et al., (2011). *PLoS One* 6(8): e22523; Andersen et al., (2012) *Nat Protoc* 7(5):891-902; Hombrink et al., (2013) *Eur J Immunol* 43(11): 3038-3050; Linnemann et al., (2013) *Nat Med* 19(11):1534-1541; Nauerth et al., (2013) *Science Translational Medicine* 5(192): 1-10; Knabel et al., (2002) *Nat Med* 8(6): 631-637; Hebeisen et al., (2015) *Cancer Res* 75(10):1983-1991; Weissbrich et al., (2013) *OncoImmunology*; Zhang et al., (2016) *Sci Transl Med* 8(341):341ra377, all of which are expressly incorporated by reference. Other methods that can be employed are described in Stronen et al., (2016) *Science* 352(6291):1337-1341.

These methods have several limitations, including the observation that the generation of $k_{off}$-rate MHC monomers that carry a reversible Strep-Tag® and a fluorescent dye cannot be combined with the UV peptide exchange strategy that these methods require. See, e.g., Weissbrich, (2015) "T cell Receptor Binding Avidity of Antigen-specific CD8+ Cytotoxic T cells in Chronic Infection," PhD Dissertation, Technical University of Munich. Specifically, it was discovered that the UV cleavable peptide in the previously-provided protocol for dye conjugated $k_{off}$-rate MHC monomers resulted in nonfunctional reagents. Despite a variety of modifications and alternative strategies to these methods, it was not possible to generate UV peptide loaded, dye conjugated MHC monomers.

Prior to the instant disclosure, the generation of these $k_{off}$-rate MHC monomers was limited to selected peptides due to the consumption of large amounts of reagents and, importantly, time. Using earlier methods, the time duration for the standard generation of one selected peptide MHC combination can require several days, with several weeks required for the synthesis of large amounts of the peptide of interest.

In the methods disclosed herein, dye conjugation of the $k_{off}$-rate MHC monomers is achieved using a maleimide reaction for covalent coupling of the dye to free, reduced cysteines. Prior to maleimide dye conjugation, the refolded and purified MHC monomer is exposed to a reducing agent, to prevent formation of disulfide bridges between the sulfhydryl (—SH) groups of a cysteine residue of a peptide antigen and a non-naturally-occurring cysteine introduced at one or more points of a MHC monomer (e.g., at the end of the MHC heavy chain or at position 67 or 88 of the light chain of a MHC 1 monomer: see Hebeisen et al., (2015) *Cancer Res* 75(10): 1983-1991; Walter et al., (1998) *J Immunol Methods* 214(1-2): 41-50).

In the previous methods using conventional peptides, the four cysteines normally present in the MHC sequence are not exposed to the surface and are therefore not affected by the reducing conditions. It has been observed that, in the presence of the UV cleavable peptide, the procedure of reduction and dye conjugation affects the stability of the MHC monomers. Thus, labels that rely on sulfhydryl chemistries for attachment to the MHC are not possible using earlier labeling methods. Indeed, prior to the disclosure of the instant methods performing these steps generated MHC monomers that were not able to associate with antigen specific T cells. Thus, what is needed is a method of increasing the stability of a UV-labile peptide loaded MHC monomer during the dye conjugation steps so as to provide detectably-labeled soluble MHC monomers loaded with a UV-labile peptide that is ready to be exchanged for a peptide of interest. The pMHC complex will then be ready to query a TCR/T cell library; conversely, a TCR/T cell will be ready to query a library of pMHC complexes created using the method.

II.a. Method of Generating a Detectably-Labeled, Soluble MHC Monomer Loaded with a Cleavable Peptide A method of generating a detectably-labeled, soluble MHC monomer loaded with a cleavable peptide is provided. The method can be used to generate a pMHC that can subsequently be used to query a library of TCRs, which can be disposed, e.g., on ex vivo T cells, TILs, T cell lines, cells transduced with a TCR gene (in which case, the T cell can be also negative for CD4 and CD8).

In the disclosed method, a labeling mixture is first formed. The labeling mixture facilitates the association of a detectable label with a MHC monomer. The labeling mixture comprises a reducing agent, which serves to prevent undesired disulfide bond formation between pMHC monomers, thus providing soluble, and not multimeric, pMHC with a cysteine residue accessible for the maleimide label. A preferred reducing agent is tris(2-carboxyethyl)phosphine (TCEP). TCEP is preferred because it does not contain a thiol group that can compete with any thiol groups of the pMHC monomers during the labeling reaction, and is more stable and effective than other reducing agents. Indeed, a problem with known labeling reactions that involve the common reducing agent dithiothreitol (DTT) is that the presence of a reactive thiol can complicate the pMHC labeling reaction; TCEP avoids this problem.

Moreover, when TCEP is used, there is no need to remove it from the reaction mixture, as is required using other reducing agents such as DTT. Indeed, an advantage of the disclosed method is the fact that there is no need to remove TCEP from the dye conjugation step of the method. This is, again, due to its lack of reactive sulfhydryl groups. The inclusion of TCEP greatly reduces the incubation periods for the labeling procedure, and the TCEP reaction can be performed simultaneously with the maleimide reaction at the same temperature and timing. This has a beneficial effect on the stability of the MHC complex.

The labeling mixture also comprises a maleimide-conjugated detectable label. Maleimide is particularly preferred in the disclosed methods due to its known chemistry, ready availability in dye-conjugated form, and its highly specific and efficient labeling ability.

Any detectable label can be used in the disclosed methods. Examples of types of detectable labels include radiolabels, fluorescent agents, chromogenic agents, chemiluminescent agents, and magnetic particles. Other types of detectable labels will be apparent upon consideration of the instant disclosure.

Due to their ease in detection and conjugation, fluorescent dyes are preferred detectable labels. Representative fluorescent dyes include an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. When selecting a fluorescent dye, size can be a consideration, and it may be desirable to avoid dyes that are comparatively larger in size, due to the fact that larger dyes can introduce steric considerations, which can create challenges for the association to TCRs on T cells.

Continuing, the labeling mixture comprises a soluble MHC monomer comprising an alpha chain and a beta chain, further comprising a non-naturally occurring cysteine residue, wherein the MHC is loaded with a cleavable peptide. As is the case with all of the disclosed methods, any class of MHC monomer can be used. When a MHC I is used, the alpha chain corresponds to the polymorphic heavy chain comprising three domains, and the beta chain corresponds to the lighter invariant beta microglobulin chain, which associates non-covalently with domain 3 of the alpha chain. When a MHC II is used, the alpha and beta chains maintain their traditional designations, as used in the literature. See, e.g., Bjorkman et al., (1987) *Nature* 329: 506-12.

The MHCs used in the method are soluble, meaning that they are not membrane bound and are present in the labeling mixture as discreet monomers, comprising an alpha and a beta chain. The presence of the reducing agent TCEP ensures that the MHCs are monomeric and not bound to one another via disulfide bonds. The term "soluble" encompasses the situation in which the MHCs are free of their natural environment (i.e., an APC cell membrane), yet may be associated with a surface, such as a welled plate. In this embodiment, although the MHCs are not free in solution and are associated with a surface, they are not membrane bound and thus soluble, as the term is used herein.

The MHCs of the method also comprise a non-naturally occurring cysteine residue. The function of this residue is to provide a known attachment point for the detectable label. Accordingly, cysteine residues can be introduced at any location of an MHC that will provide a suitable site for reaction and conjugation with the detectable dye without interfering with the MHC conformation.

When a MHC I is used in the method, preferred sites of non-naturally occurring cysteine incorporation include one or both of (a) position 67 or 88 of the MHC I beta chain; and (b) the C-terminus of the MHC I alpha chain. Other MHC I incorporation sites can be readily determined and form an aspect of the disclosure. When a MHC II is used in the method, preferred sites of non-naturally occurring cysteine incorporation include one or both of (a) the C-terminus of the MHC II beta chain; and (b) the C-terminus of the MHC II alpha chain. Similarly, other MHC II incorporation sites can be readily determined and form an aspect of the disclosure.

A soluble MHC of the disclosed methods comprises a cleavable peptide. The presence of the cleavable peptide serves to stabilize the soluble MHC, since the MHC comprises two distinct chains which will dissociate without the stabilizing effect of the cleavable peptide. There is no limit on the composition or length of a cleavable peptide, except that the peptide should fit the binding groove of the MHC with which it is associated (15-24 residues for a MHC 2, and 8-10 residues for a MHC 1).

The cleavable peptide can comprise one or more non-naturally occurring amino acids, which can facilitate the binding of the peptide to the MHC. For example, norleucine and other analogs of the twenty naturally-occurring amino acids can be incorporated into a cleavable peptide and can be selected based on the presence and identity of reactive side groups. For example, it may be preferable for a cleavable peptide to feature a hydroxyl or other reactive side chain.

Cleavable peptides are, by definition, cleavable and separable from their MHCs. The method of cleavage employed will depend on chemistry of the non-naturally occurring cleavable amino acid, and examples of methods of cleaving a peptide include chemical means, oxidation pH changes, enzymatic cleavage and most preferably, UV light-mediated cleavage.

Continuing with the method, the labeling mixture comprising the TCEP, the maleimide conjugated detectable label and the soluble pMHC is then incubated at a desired incubation temperature a desired incubation period. The incubation temperatures and times can be empirically optimized for a given set of components. In specific embodiments, and as demonstrated in the Examples that follow, the incubation period is less than about 2.5 hours and the incubation temperature is about room temperature (about 20-24° C.). In other embodiments the incubation temperature is 4° C. and the incubation time is about 12 hours.

Finally, any unbound maleimide-conjugated detectable label is removed from the labeling mixture. By removing unbound label background signal can be minimized when the labeled MHC is used in subsequent applications, such as those disclosed herein. The removal can be accomplished by, e.g., dialyzing away unbound label, washing away unbound label when the reaction is performed on a substrate such as a gel filtration column, welled plate, filtration through a membrane (e.g., in a dialysis-type approach), precipitation, etc.

At the conclusion of the method, a detectably-labeled, soluble MHC monomer is produced. MHCs generated using the disclosed method form an aspect of the disclosure. Such MHCs can be used, for example, to query TCR libraries with a peptide of interest, following exchange of the cleavable peptide with the peptide of interest.

II. b. Method of Identifying a TCR that Associates with a MHC-Peptide Complex

In another aspect, a method of identifying a TCR of interest that associates with a MHC-peptide complex is provided. The method relies on a detectably-labeled, soluble MHC monomer loaded with a cleavable peptide prepared as described above in section II.a. and the Examples, and provides a rapid and efficient method for the identification of a TCR that recognizes a particular pMHC with a desired avidity. As is the case with all methods of the instant disclosure, and one advantage of the disclosed methods, peptides non-covalently associated with a MHC that can be used in the method can comprise a cysteine residue.

A labeled pMHC generated as described herein will have a cleavable peptide associated with the MHC. The cleavable peptide serves as a mere structural aid and not as a peptide with which to query a TCR. It is known that without a peptide present, i.e., the cleavable peptide, the MHC complex is not stable and will be dissociated. Thus, when MHC monomers are studied they employ a peptide or other molecule to stabilize the complex during experiments. In the methods disclosed herein, the cleavable peptide serves this function.

Next, the cleavable peptide is exchanged with a peptide of interest. The peptide of interest, as noted herein, can be a cysteine peptide and comprise a cysteine residue and can be derived from any source. For example, a peptide of interest can be derived from a tumor antigen. In other examples, a peptide of interest can comprise a peptide which is not known to be a relevant antigen, and can be designed to test the peptide for T cell binding. In other embodiments, a peptide of interest can comprise a peptide known or suspected to comprise a neo antigen. For an identified specific TCR, a peptide of interest can compromise variants of the peptide to query the TCR's cross-reactivity. In the context of the disclosed method the peptide of interest functions as the subject of a TCR binding query.

The cleavable peptide disrupted and released from the MHC using any method for which the peptide is adapted. For example, as described herein and in the literature, a common and preferred method of cleaving a peptide is by the use of UV light. Depending on the nature of the bond in the cleavable amino acid of the peptide, UV light in the range of about 350 nm to about 400 nm is preferred for initiating the exchange of peptides, with UV light of about 366 nm more preferred. Other methods to facilitate the exchange can also be employed, such as chemical or oxidative cleavage, changes in pH and enzymatic cleavage.

Following exchange of the cleavable peptide with the peptide of interest, a kinetic property of the MHC-peptide-TCR complex selected from the group consisting of $K_{off}$, $K_{on}$, and $K_D$, wherein the kinetic property indicates a degree to which a TCR associates with the MHC-peptide complex, is determined.

The labeled pMHCs can be used as monomers and/or to form a MHC multimer complex. The multimers will comprise a plurality of pMHC molecules. As is the case with all the methods disclosed herein, in various embodiments the MHC can be used in high local concentrations, disposed in a non-naturally occurring environment such as a lipid bilayer, associated with a surface such as a welled plate, or on a cell or a bead that does not normally express a MHC. Without the formation of multimers comprising pMHC molecules, association of soluble pMHCs to TCRs expressed on T cells is limited by low affinity interactions, and the TCR-pMHC complexes will not be stable. Thus, by forming multimers a stable association between the complexes and the TCRs can be generated.

Figure 3A:
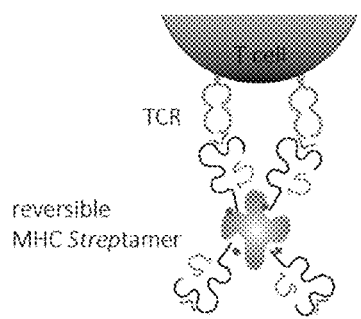
FIGS. 3A to 3C are a series of three cartoons depicting a representative TCR ligand $k_{off}$-rate assay for identifying TCRs using pMHC complexes generated using the disclosed methods.
Figure 3B:
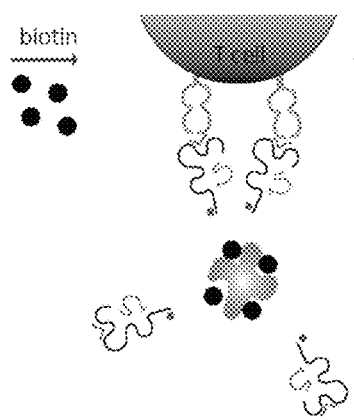
Figure 3C:
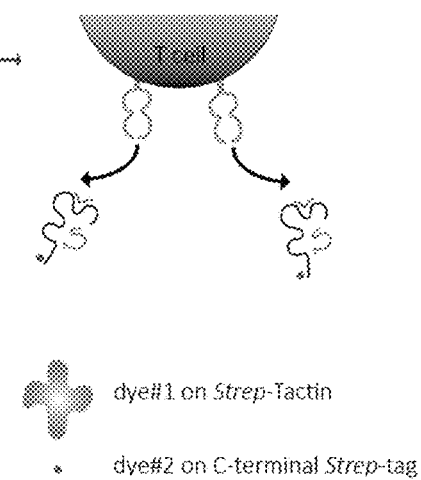

One method for forming reversible multimeric complexes involves the association of the MHCs with a backbone molecule, such as Strep-Tactin®. See, e.g., Knabel et al., (2002) Nat Med 8(6): 631-637, and FIG. 3A. In this embodiment, the pMHC will be tagged with a Strep-Tag®, allowing the MHC to associate with the Strep-Tactin® backbone. When the Strep-tagged MHC is contacted with the Strep-Tactin® backbone, which has multiple association sites for the Strep-Tags®, multimers of pMHCs are formed at various attachment points on the Strep-Tactin® backbone. Other methods of forming pMHC multimers are known and can be employed in the step of the disclosed method (see, e.g., Tischer et al., (2012) Int Immunol 24(9): 561-572; US Patent Application US 2013/0289253).

At this point in the method, pMHC monomers and/or multimers of pMHC complexes will be present, possibly associated with a backbone or support structure. The multimers are then contacted with a TCR library under conditions that allow the formation of a MHC-peptide-TCR complex. The TCR library can comprise, for example, ex vivo T cells, tumor infiltrating lymphocytes (TILs), in vitro expanded T cells, cells transduced with a TCR gene, etc. In the case that the T cell library comprises T cells transduced with a TCR gene, the T cell can optionally also be negative for CD4 and CD8. In essence, a TCR library will comprise TCRs for which it is desired to identify those which bind to a pMHC complex of interest with a preferred degree of avidity. As is the case with the pMHCs of the disclosed methods, TCRs can also exist as recombinantly-expressed chains disposed on a structure such as a membrane, which can itself be associated with a non-biologic structure such as a welled plate, culture support or a similar structure, or even just associated with the structure itself (i.e., recombinantly-expressed chains associated with a structure, but in the absence of a membrane).

The pMHCs are contacted with the TCR library under conditions that permit, and are favorable to, the formation of TCR-pMHC complexes. Suitable conditions are known and are described in the literature (see, e.g., Nauerth et al., (2013) Expert Rev Clin Immunol 9(12): 1151-1153; Rodenko et al., (2006) Nat Protoc 1(3): 1120-1132; Khilko et al., (1995) J Immunol Methods 183(1): 77-94; Knabel et al., (2002) Nat Med 8(6): 631-637; Wooldridge et al., (2009) Immunology 126(2): 147-164; Huppa et al., (2010) Nature 463(7283): 963-967; Andersen et al., (2012) Nat Protoc 7(5): 891-902; Dolton et al., (2015) Immunology 146(1): 11-22; Hebeisen et al., (2015). Cancer Res 75(10): 1983-1991; Zhang et al., (2016) Sci Transl Med 8(341): 341ra377) and can comprise, for example TCRs on T cells suspended in a small volume of about 50 ul physiological, non-toxic buffers (PBS pH 7.4 including 10% Fcs and 1 mM EDTA) in the presence of pMHCs.

During the contacting of the previous step in the method, complexes comprising TCRs and pMHCs may form due to recognition of the peptides presented by the MHCs to the TCR. Non-binding pMHCs can optionally be removed from the local environment of the TCR library, leaving only those pMHCs that associate with TCRs. If desired, the removal can be accomplished by washing away non-associated pMHCs (e.g., washing unbound pMHCs away from TCRs of a T cell library).

At this point in the disclosed method only pMHCs complexes that are associated with TCRs, to some degree will be present. In order to identify those pMHCs (and conversely TCRs) with a preferred binding capability, the multimer complexes are disrupted. When Strep-Tactin® is used as a multimerization scaffold, biotin can be used to disrupt the multimers and release the multimerization scaffold from the pMHCs associated with TCRs. This leaves any pMHCs recognized by a TCR temporarily associated with the TCR.

Finally, the MHC-peptide-TCR $K_{off}$ is determined ($K_{off}$ is $K_{off}$ or $K_{3D}$, representing the kinetics of the ternary complex), and can be calculated by monitoring the signal change of a labeled pMHC as it dissociates from a TCR as a function of time. See, e.g., Nauerth, Weissbrich, Knall et al., (2013) Sci. Trans. Med. 5(192): 1-10; Hebeisen et al., (2015) Cancer Res 75(10): 1983-1991. The rate of change of the signal can be measured using any convenient method and will be a function of the nature of the detectably label selected for labeling the MHCs. For example, when a fluorescent label is used to label MHCs, real time microscopy or flow cytometry can be used to determine the kinetic property (examples of these techniques are described in Nauerth et al., (2013) Science Translational Medicine 5(192): 1-10; Hebeisen et al., (2015) Cancer Res 75(10): 1983-91), and the decay rate of fluorescent signal as a function of time can be monitored. This decay rate ($K_{off}$) directly correlates with the dissociation of labeled pMHC from TCR.

Alternatively, the build-up of fluorescent signal ($K_{on}$) can also be monitored and reflects the association of a pMHC with a TCR. Methods for monitoring fluorescence signal build-up are known (see, e.g., Li et al., (2006) J Biol Chem 282(9):6210-21), and can be employed in the method. Based on $K_{off}$ and $K_{on}$ values, the $K_D$ can then be calculated ($K_D=K_{off}/K_{on}$).

One method for measuring association ($k_{on}$-rate) times of pMHC monomers to TCR libraries is based on high local concentrations of labeled MHC monomers and TCRs (e.g., expressed on the T cell surface). In one embodiment, specific T cells can be purified (e.g., FACS or MACS purification) before measurement. In another embodiment, specific T cells, e.g., ex vivo isolated, in vitro expanded or TCR transduced T cells in a cell mix, are specifically labeled. Examples for specific labels include irreversible MHC multimers, antibodies specific for TCR constant or TCR variable region. The pMHC monomers are then contacted with a TCR library under conditions that allow the formation of a MHC-peptide-TCR complex. The TCR library can comprise, for example, ex vivo T cells, tumor infiltrating lymphocytes (TILs), cells transduced with a TCR gene, etc. In the case that the T cell library comprises T cells transduced with a TCR gene, the T cell can optionally also be negative for CD4 and CD8. In essence, a TCR library will comprise TCRs for which it is desired to find those which bind to the pMHC complex with a preferred degree of avidity. TCRs can also exist as recombinantly-expressed chains disposed on a structure such as a membrane, which can itself be associated with a non-biologic structure such as a welled plate or a similar structure, or even just with the structure itself (i.e., recombinantly-expressed chains in the absence of a membrane).

The pMHCs are contacted with the TCR library under conditions that permit, and are favorable to, the formation of TCR-pMHC complexes. Suitable conditions are known and are described in the literature (see, e.g., Nauerth et al., (2013) *Expert Rev Clin Immunol* 9(12): 1151-1153; Rodenko et al., (2006) *Nat Protoc* 1(3): 1120-1132; Khilko et al., (1995) *J Immunol Methods* 183(1): 77-94; Knabel et al., (2002) *Nat Med* 8(6): 631-637; Wooldridge et al., (2009) *Immunology* 126(2): 147-164; Huppa et al., (2010) *Nature* 463(7283): 963-967; Andersen et al., (2012) *Nat Protoc* 7(5): 891-902; Dolton et al., (2015) *Immunology* 146(1): 11-22; Hebeisen et al., (2015). *Cancer Res* 75(10): 1983-1991; Zhang et al., (2016) *Sci Transl Med* 8(341): 341ra377) and can comprise, for example TCRs on T cells suspended in a small volume of about 100 ul physiological, non-toxic buffers (PBS pH 7.4 including 10% Fcs and 1 mM EDTA). Typically, $K_{on}$ is the $K_{on}$ observed at a given concentration of pMHC. Suitable concentration of pMHC may range from about 1-50 µM, 5-40 µM, 10-30 µM, 12-25 µM, or 14-20 µM. In some embodiments, suitable concentration of pMHC may be at or greater than about 2 µM, 4 µM, 6 µM, 8 µM, 10 M, 12 µM, 14 µM, 16 µM, 18 µM, or 20 µM.

In order to identify those pMHC (and conversely TCRs) with a preferred binding capability, the MHC-peptide-TCR $K_{on}$-rate (in this case $K_{on}$ is $K_{on}$ or K3D representing the kinetics of the ternary complex) of pMHC monomers can be calculated by monitoring the signal change of a labeled pMHC as it associates to the specific TCRs as a function of time. The rate of change of the signal can be measured using any convenient method and will be a function of the nature of the detectable label selected for labeling the MHCs. For example, when a fluorescent label is used to label MHCs, real time microscopy or flow cytometry can be used to determine the kinetic property.

Ultimately, the kinetic parameter will be an indicator of the avidity of a given pMHC for a given TCR. A cut-off value can be chosen, below which a given TCR can be considered to not strongly associate with a given pMHC. In preferred embodiments, a half-life time $(t_{1/2} 32 \ln(2)/K_{off})$ of about 15 seconds or longer can be used as an indication that a pMHC and a TCR associate strongly. In a more preferred embodiment, a half-life time of between about 15 and about 500 seconds indicates that a pMHC and a TCR associate strongly. TCR-pMHC pairs that fall within the selected $K_{off}$ range (i.e., those in which the TCR and pMHC, and optionally CD4 or CD8, associate) can be selected, indicating that the TCR of the pair is of interest for further study or use. Other preferred $K_{off}$ rates include 15, 20, 30, 40, 50, 60, 70, 80, 90, 100, 200, 300 and 400 seconds. Preferred $K_{off}(K_{3D})$ rates for TCR-pMHC-CD4/CD8 complexes include 15, 20, 30, 40, 50, 60, 70, 80, 90, 100, 200, 300, 350 and 400 seconds. Additionally or alternatively, $K_{on}$-rate can be used as an indicator of binding between a pMHC and a TCR. Typically, $K_{on}$-rate (or K3D) of pMHC monomers measured according to the present invention about 50 seconds or less can be used as an indication that a pMHC and a TCR associate strongly (e.g., about 10, 20, 30, 40, 45, 46, 47, 48, 49, 50 seconds using a suitable concentration of pMHC described herein (e.g., 16 µM)).

Applications for TCRs identified using the disclosed methods are numerous. For example, TCRs found to associate with a pMHC to a desired degree (e.g., having a half-life time $(t_{1/2}=\ln(2)/K_{off})$ of between about 20 and about 500 seconds, and/or an observed $K_{on}$ rate of less than 50 seconds, or a stable binding of MHC monomers) can be cloned and a receiving cell can be transduced with a nucleic acid encoding the TCR alpha, beta or both alpha and beta sequences identified. Such a cell can be a T cell that expresses endogenous TCR genes, a T cell that does not express endogenous TCR genes (such coding sequences may have been knocked out or expression suppressed), or a cell other than a T cell that does not express endogenous TCR genes such as a dendritic cell or other immune cell (i.e., a cell that has been transduced with TCR alpha and/or beta encoding sequences). Examples of cells include central memory T cells, effector memory T cells, naive T cells from peripheral blood, T cells from lymph nodes, or T lymphocyte progenitor cells from bone marrow. When a T cell is selected for this application, the T cell can express a CD4 molecule, or a CD8 molecule depending on the nature of the T cell selected (e.g., T helper, T cytotoxic, etc.). Other cells that can be engineered to express TCRs of interest include cells generated from artificial thymus organoids (ATOs) and other systems for generating allogeneic cells.

The method can be particularly useful for identifying TCRs that bind antigenic peptides of interest, such as neo antigens which have been extracted from biologic samples (e.g., tumor samples). Moreover, the method can be performed at a temperature of between about 4° C. and about 37° C., for example about 20° C., making the method convenient to perform at room temperature.

II.c. Method of Selecting a T Cell Suitable for Adoptive Transfer

In another aspect, the disclosed methods can be used to select a T cell suitable for adoptive therapy. In adoptive therapy, T cells directed against antigens expressed by neoplastic cells are administered to a patient. T cells suitable for adoptive transfer will be cells that express TCRs that associate with a given antigenic peptide of interest, when presented by an MHC, and thus will have anti-tumor reactivity. Antigenic peptides of interest include neo antigens. With the goal of selecting a T cell suitable for adoptive transfer in mind, a method to accomplish this aim is provided.

Initially, the method involves performing the steps outlined above in section II.b., which will provide a TCR of interest that exhibits a desirable kinetic property for the purpose of adoptive therapy. These TCRs can be selected based on a set of predetermined criteria. As a guideline, for adoptive therapy it is generally desirable that TCRs with a somewhat higher avidity and/or a slower off-rate and/or faster on-rate for a pMHC complex for that complex are selected (e.g., TILs).

In this embodiment of the instant disclosure the TCRs will be disposed on T cells, which can be in suspension or associated with a substrate such as a welled plate, a cell culture support, etc.

For purposes of adoptive transfer, a TCR of interest will associate with a peptide derived from a tumor cell and present as a component of a pMHC complex, and will have a $K_{off}$ as determined by the method described in section II.b. $(t_{1/2}=\ln(2)/K_{off})$ of between about 15 seconds and about 500 seconds and an observed $K_{on}$-rate of less than 50 seconds at 16 µM.

In one aspect, the disclosed methods can be used to identify T cells expressing TCRs of interest, which can themselves be administered to a subject in need thereof, as adoptive T cell therapy. The subject will have a matched HLA allele and tumor cells that express an antigenic protein that is recognized by T cells expressing TCRs, as selected using the methods described herein. For this purpose the methods can comprise additional steps, as described below.

Following the selection of a suitable T cell, the T cell is expanded to a population of at least $1\times10^2$ T cells. The expansion of T cells can be achieved by activating them using any desired activation method. For example, expansion can be achieved by employing OKT3 antibodies, Dynabeads® coated with anti-CD3 and anti-CD28 antibodies, contact with IL2, IL4, ConA, PHA, PMA or a combination thereof, or any other known method.

After the T cells have been expanded to a count of at least $1\times10^2$ cells, a desired number of cells can be administered to a subject. The exact number of cells can vary but will not be less than $1\times10^2$ cells. In embodiments, $1\times10^2$, $1\times10^3$, $1\times10^4$, $1\times10^5$, $1\times10^6$ cells, $1\times10^7$ $1\times10^8$, $1\times10^9$, $1\times10^{10}$ cells, or more cells can be administered to a subject.

II.d Method of Identifying a Member of a Binding Pair of Interest

The disclosed methods have broad and general applicability and can be used to study the interaction between any two binding partners. The binding partners can comprise a receptor and ligand pair, or a pair of proteins known or suspected to associate with one another. In another aspect, the binding partners can comprise a protein and a nucleic acid such as DNA or RNA. Thus, in still another embodiment, a method of identifying member of a binding pair of interest is provided.

In the disclosed method, a labeling mixture is first formed. The labeling mixture facilitates the association of a detectable label with a first member of a binding pair. The labeling mixture comprises a reducing agent, which serves to prevent undesired disulfide bond formation. A preferred reducing agent is tris(2-carboxyethyl)phosphine (TCEP).

As noted herein, TCEP is preferred because it is more stable and effective than other reducing agents and addresses a problem with known labeling reactions that involve the common reducing agent dithiothreitol (DTT), namely that the presence of a reactive thiol can complicate the labeling reaction. Moreover, when TCEP is used, there is no need to remove it from the reaction mixture, as is required using other reducing agents such as DTT. Indeed, an advantage of the disclosed method is the fact that there is no need to remove TCEP from the dye conjugation step of the method. This is, again, due to its lack of reactive sulfhydryl groups. The inclusion of TCEP greatly reduces the incubation periods for the labeling procedure, and the TCEP reaction can be performed simultaneously with the maleimide reaction at the same temperature and timing.

The labeling mixture also comprises a maleimide-conjugated detectable label. Maleimide is particularly preferred in the disclosed methods due to its known chemistry, ready availability in dye-conjugated form, and its highly specific and efficient labeling ability. Any detectable label can be used in the disclosed methods. Examples of types of detectable labels include radiolabels, fluorescent agents, chromogenic agents, chemiluminescent agents, and magnetic particles. Other types of detectable labels will be apparent upon consideration of the instant disclosure. Due to their ease in detection and conjugation, fluorescent dyes are especially preferred detectable labels. Representative fluorescent dyes include an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. When selecting a fluorescent dye, size can be a consideration; it may be desirable to avoid dyes that are comparatively larger in size, due to the fact that larger dyes can introduce steric considerations, which can create challenges for the labeling process.

The labeling mixture comprises a first member of a binding pair. As noted herein, a binding pair can comprise any two molecules known or suspected to interact and associate. For example a binding pair can comprise a traditional receptor-ligand pair, such as the interaction between surface expressed adhesion molecules ICAM-1 and LFA-1 or L-selectin and its ligand PSGL-1. Alternatively, a binding pair can comprise a protein and a nucleic acid, such as DNA and a DNA binding protein. A binding pair can also comprise RNA and a RNA binding protein. In yet another embodiment, a binding pair can comprise two proteins, neither of which is a traditional receptor. Examples of proteins that can comprise a binding pair include, antibodies and antigens, peptides and MHCs, and scFv's (e.g., as a component of a CAR) and a cell surface protein (e.g., a CAR's ligand). In a preferred embodiment, a binding pair comprises a receptor and a ligand, and the ligand is labeled by the described labeling process. Continuing, the labeling mixture comprising the TCEP, the maleimide conjugated detectable label and the first member of a binding pair is then incubated at a desired incubation temperature a desired incubation period. The incubation temperatures and times can be empirically optimized for a given set of components. In specific embodiments, the incubation period is less than about 2.5 hours and the incubation temperature is about room temperature (about 20 to about 24° C.). In other embodiments the incubation temperature is 4° C. and the incubation time is about 12 hours.

Finally, any unbound maleimide-conjugated detectable label is removed from the labeling mixture. By removing unbound label background signal can be minimized when the labeled binding partner is used in subsequent applications, such as those disclosed herein. The removal can be accomplished by, e.g., dialyzing away unbound label, washing away when the reaction is performed on a substrate such as a gel filtration column, welled plate, filtration through a membrane (e.g., in a dialysis-type approach), precipitation, etc. At the conclusion of the method, a detectably-labeled first member of a binding pair is produced.

The one member of a binding pair, which is now labeled, is contacted with a screening library comprising a known or suspected second member of the binding pair under conditions that allow the formation of an association complex. The screening library comprises a plurality of molecules known or suspected to associate with the labeled first binding pair member. The nature of the screening library will be dictated by the nature of the labeled member of the binding pair. For example, if a ligand is labeled, the screening library can comprise a plurality of receptors known or suspected to bind to the ligand, such as a library of TCRs or pMHCs. Alternatively, if a protein-protein interaction is of interest, the screening library can comprise antibodies or antigens, etc. Other examples of screening libraries include collections of DNA or RNA.

The conditions that allow the formation of an association complex will also vary with the nature of the members of the binding pairs. Considerations include pH, the presence or absence of ionic species, the hydrophobicity of the local environment of the members of the library, the temperature at which the contacting is performed, the duration of the contacting, concentration of the binding pair, total volume, etc.

Finally, the presence or absence of an association complex is detected. The detection will depend on the nature of the label used. For example, when a fluorescent label is used, which is a preferred embodiment, a fluorescent signal can be detected. Other methods of detecting the presence or absence of an association complex will be known to those of skill in the art.

Optionally, any association complex that is formed by performing the disclosed method can be further analyzed. Thus, the method can further comprise the step of determining a kinetic property of an association complex comprising the first and second members of the binding pair is determined, the kinetic property being selected from the group consisting of a $K_{off}$ and $K_{on}$, wherein the kinetic property indicates a degree to which the first member of the binding pair associates with the second member of the binding pair (which can be a binary pMHC complex, making $K_{off}$ representative of $K_{3D}$). $K_{off}$ and $K_{on}$ are described herein and can be calculated as a function of the detection method (e.g., time for an association complex to form or dissociate, etc.).

INCORPORATION BY REFERENCE

All publications, patents, and patent applications mentioned in this specification are herein incorporated by reference to the same extent as if each individual publication, patent, or patent application was specifically and individually indicated to be incorporated by reference. The citation of a reference herein should not, however, be construed as an acknowledgement that such reference is prior art to the disclosed invention(s). To the extent that any of the definitions or terms provided in the references incorporated by reference differ from the terms and discussion provided herein, the terms and definitions provided herein control.

The foregoing description is considered to be sufficient to enable one skilled in the art to practice the invention. The foregoing description and Examples that follow detail certain preferred embodiments of the invention and describe the best mode contemplated by the inventor. It will be appreciated, however, that no matter how detailed the foregoing may appear in text, the invention may be practiced in many ways and the disclosed invention(s) should be construed in accordance with the appended claims and any equivalents thereof.

The present invention is further illustrated by the following examples which should not be construed as further limiting. The contents of all references cited throughout this application are expressly incorporated herein by reference.

EXAMPLES

The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook et al., *Molecular Cloning: A Laboratory Manual*, 2nd ed., Cold Spring Harbor Laboratory Press (1989) and Coligan et al., *Current Protocols in Immunology*, Wiley & Sons, Incorporated (2007).

Example 1

Labeled MHC I Monomers

Conventional fluorescence labeled MHC monomers were generated as described in (Nauerth et al., (2013) *Science Translational Medicine* 5(192):1-10). Briefly, the human MHC beta chain and the MHC alpha HLA-A*02:01 chain with the Strep-Tag® III sequence fused to a glycine-serine linker and a cysteine were expressed in *Escherichia coli* strains, purified and refolded at high dilution in the presence of peptide. Peptide loaded MHC monomers were purified by gel filtration (Enrich SEC 650, BioRad) and incubated overnight with 0.1 mM dithiothreitol (DTT) to reduce accessible cysteine residues for maleimide conjugation. Buffer was exchanged to PBS pH 7.3 for maleimide-dye conjugation in a 10:1 molar ratio for 2 h at room temperature. Labeled pMHC monomers were purified from unbound label by gravity flow columns (illustra NAP-25 columns, GE Healthcare).

UV-exchange peptide loaded MHC monomers were generated accordingly by refolding of MHC beta chain and MHC HLA-A*02:01 alpha chain and in the presence of the UV-labile peptide (a cleavable peptide) and subsequent gel filtration purification. For labeling, the peptide loaded MHC monomers were incubated with 0.1 mM tris(2-carboxyethyl) phosphine (TCEP) for reduction of accessible cysteine residues, in the presence of the maleimide label in a 10:1 molar ratio for 2 h at room temperature. Labeled pMHC monomers were purified from unbound label by gravity flow columns (illustra NAP-25 columns, GE Healthcare). 50 µl of 0.1 mg/ml refolded UV-exchange peptide MHC monomer in the presence of 50 µM test peptide were exposed for 1 h at 4° C. to 366 nm UV light (CAMAG UV Cabinet) as described for biotinylated, non-labeled MHC monomers in (Rodenko et al., (2006) *Nat Protoc* 2006. 1(3):1120-32).

Example 2

Staining of T Cells

Combinatorial, irreversible MHC multimer staining was performed as previously described (Andersen et al., (2012) *Nat Protoc* 7(5): 891-902) using UV-exchanged, biotinylated HLA-A*02:01 molecules loaded with the same peptide and multimerized on Streptavidin APC or PE.

For formation of the reversible MHC Streptamer complex, about 1 ug of conventional refolded, labeled MHC monomer or 3-4 ug of UV-exchange peptide MHC monomers exchanged against the test peptide was incubated for about 45 min with 5 ul (0.75 ug) of IBA Strep-Tactin APC in 50 μl PBS.

T cells were washed in PBS containing 10% BSA, EDTA and 0.09% azide at 4° C., cooled for about 20 min on ice and subsequently about $1\times10^6$ to $5\times10^6$ cells were suspended in either 20 ul of MHC Streptamer solution consisting of conventional MHC monomers or 50 ul of UV-peptide exchanged MHC Streptamers. Cells were stained for 45 minutes on in the presence of anti-CD4 and/or anti-CD8 fluorescence conjugated antibodies and live-dead staining reagent during the last 20 min before washing and analysis on the flow cytometer (BD Fortessa).

Example 3

TCR-Ligand $k_{off}$-Rate Measurement by Flow Cytometry

About $1\times10^4$ to $1\times10^5$ MHC Streptamer and antibody stained T cells were diluted into 0.5 ml of about 20° C. cold PBS, containing 10% BSA, EDTA, 0.09% azide, into a FACS tube mounted on a temperature control device (qutools). Acquisition was started for 30 s, 0.5 ml of 2 mM d-biotin was added to the sample to tube to disrupt the MHC Streptamer and initiate the MHC monomer dissociation that was followed for 10 min at about 20° C. FACS data plots were analyzed using FlowJo® software by exporting mean fluorescence intensities of MHC monomer label over the time into GraphPad Prism® software to fit an exponential decay curve and calculate $k_{off}$-rate and half-life time.

Example 4

Cysteine Residues in Test Peptides Loaded on MHC Abolish TCR Ligand $K_{off}$-Rate Measurement During the labeling procedure of MHC monomers for TCR ligand $K_{off}$-rate measurement, free accessible cysteine residues covalently bind to maleimide label. If the antigenic peptide of interest contains a cysteine that is exposed to the surface, it will be conjugated to the maleimide label, as depicted in FIG. 4A. Residues in the peptide that are exposed to the surface are also likely to be recognized by a specific TCR. Consequently, a modification, such as the maleimide label, of a cysteine in the peptide on the MHC can interfere with the TCR binding to the pMHC complex as depicted in FIG. 4B.

Two different TCRs specific for a 9-mer HLA-A*02:01 peptide containing a cysteine at position 8, TCR #1 and TCR #2, were tested. A high proportion of T cells transduced with the TCR #1 and TCR #2 was stained with MHC multimers consisting of biotinylated, non-labeled MHC monomers and Streptavidin backbone (35% and 44% of living CD8+ lymphocytes, respectively, as shown in FIG. 4C). In contrast, a staining of the transduced T cells with MHC Streptamers consisting of reversible, labeled MHC monomers and Strep-Tactin® (IBA Life Sciences) backbone was absent due to the cysteine modification of the peptide loaded on the MHC monomers, as shown in FIG. 4D.

Figures 5A, 5B, 5C:
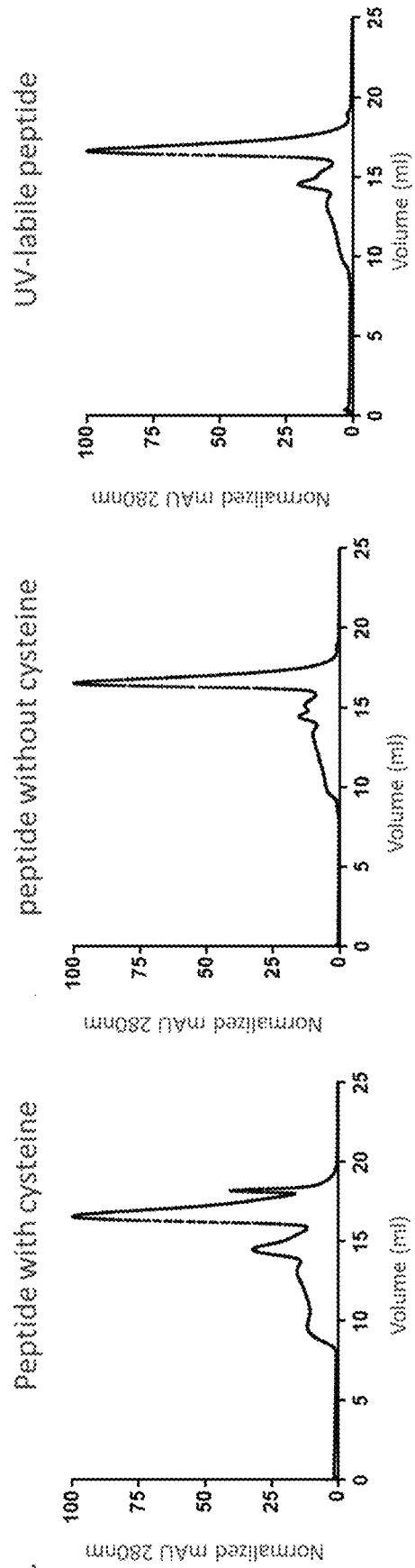
FIGS. 5A to 5C are a series of plots showing SEC results highlighting proper pMHC folding before labeling using the known methods in the presence of different peptides; containing a cysteine residue (FIG. 5A; peptide with cysteine), a peptide containing no cysteine residue (FIG. 5B; peptide without cysteine) and atypical UV-labile peptide (FIG. 5C), occurring when the peptides were labeled using known methods.

The profiles in the size exclusion chromatography after the refolding of the purified MHC alpha HLA-A*02:01 chain and the beta chain in the presence of the indicated peptide for this non-functional MHC monomer loaded with the peptide containing a cysteine (as shown in FIG. 5A) was comparable to the profile of a functional, labeled MHC monomer loaded with a peptide without cysteine (as shown in FIG. 5B), as well as to the profile of the MHC monomer loaded with the UV-labile peptide (as shown in FIG. 5C), indicating that the MHC monomers after refolding were functional but modified after the size exclusion.

Example 5

Figure 6:
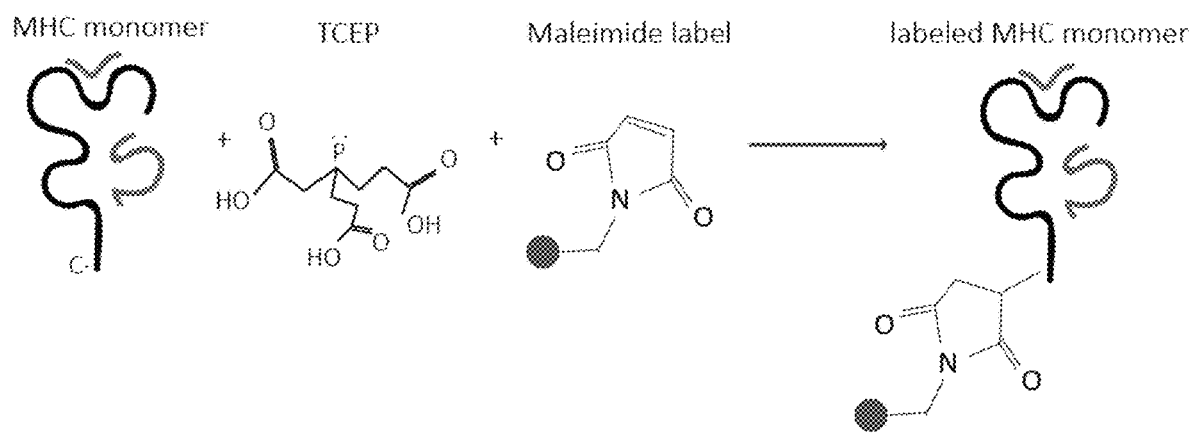
FIG. 6 is a cartoon showing a schematic of a labeling process provided herein.

Development of a Labeling Procedure for Stable and Functional UV-Labile Peptide-Loaded MHC Monomers Driven by limitations in known methods, a method was successfully developed by which a peptide containing a cysteine could be replaced on the MHC monomer after the labeling preventing any modification of the cysteine. Specifically, because standard maleimide labeling procedures for conventional peptide-loaded MHC monomers for the TCR ligand $K_{off}$-rate measurement was interfering with the stability and function of the UV-labile peptide loaded MHC monomer, a procedure was developed that allows to label MHC monomers loaded with UV-labile peptides. To this end, the previously used reducing agent DTT was replaced by TCEP to prepare SH-groups of cysteine residues on the MHC monomers for maleimide conjugation. In contrast to DTT, TCEP was used without pre-incubation, but in the presence of the maleimide label during the labeling procedure of the MHC monomers with the non-natural cysteine residue, as depicted in FIG. 6. The incubation time of the UV-peptide loaded MHC to the reducing agents as compared to previous DTT-based procedures could be reduced six-fold.

To test whether the MHC monomers loaded with the UV-labile peptide labeled using the improved methods described herein and in this Example could still recognize a TCR, UV-peptide exchange was performed on biotinylated, non-labeled MHC monomers, as well as on the Strep-tagged, labeled MHC monomers.

Using standard procedures (Andersen et al., (2012) Nat Protoc 7(5): 891-902), irreversible MHC multimers with two different fluorescent dyes #1 and dye #2 were generated and used to stain peptide specific T cells, depicted in FIGS. 7A and 7D. Conventionally refolded (in the presence of the peptide of interest to form pMHCs), labeled MHC monomers were multimerized according to standard procedures (Knabel et al., (2002) Nat Med 8(6): 631-637; Nauerth et al., (2013) Science Translational Medicine 5(192): 1-10) and the staining was compared to that of multimers formed by using the peptide-exchanged, labeled MHC monomers (results shown in FIGS. 7B, 7C and 7E). When using a three-fold access of UV-peptide exchanged, labeled MHC monomers either during the exposure to UV light or after UV peptide exchange for the multimerization on Strep-Tactin® backbone, the MHC Streptamer® staining (FIG. 7E right) was similar to MHC Streptamer staining using conventional labelled MHC monomers according to standard protocol (FIG. 7E left). The frequency of stained TCR transduced T cells with MHC Streptamer was comparable to stainings using biotinylated MHC multimers (FIG. 7D). The standard concentration for UV-peptide exchange of labeled MHC monomers was too low to form a functional MHC Streptamer complex and no staining was detected. Similar results were obtained using two other peptides in the context of HLA-A*02:01 for the staining of specific T cells.

As a next step to test the functionality of the labeled, UV-peptide exchanged MHC monomers prepared using the disclosed method, the dissociation of the MHC monomers upon disruption of the multimeric complex by biotin was tested by flow cytometry, the results of which are shown in FIG. 8. The intensity of the dye conjugated to the MHC monomers is plotted against the time of acquisition using conventional labelled MHC monomers (FIG. 8A) or labelled, UV exchanged MHC monomers (FIG. 8B). The initial 30 seconds show the dim staining of MHC monomers in the Streptamer complex. After 30 seconds, d-biotin was added to the sample tube and the MHC monomer intensity increased due to the dissociating Strep-Tactin® that no longer quenched the MHC dye.

Both dissociation curves for the conventional refolded and labeled MHC monomer and the UV-peptide exchanged MHC monomer were comparable in the dot plot (FIG. 8A-B), as well as upon extracting the mean fluorescence intensities and fitting the exponential decay curve for calculation of the half-life time (t1/2) of the TCR with the respective pMHC ligand, shown in FIGS. 8C and 8D.

In addition to the peptide "A"-specific TCR analyzed in FIG. 8, the TCR ligand $K_{off}$-rate was determined using conventional or UV-peptide exchanged, labeled MHC monomers of two other TCRs expressed on PBMCs specific for the peptides "X" and "Y", respectively. The half-life times using the novel UV-peptide exchanged MHC monomers for all three TCRs with distinct peptide specificities were comparable to the values measured with conventional refolded and labeled MHC monomers as shown in the bar chart of FIG. 9, indicating that the functionality of MHC monomers generated with the disclosed method are functional.

Example 6

UV-Peptide Exchange of Labeled MHC Monomers Enables the Characterization of T Cells Specific for Cysteine-Containing Peptides in the TCR Ligand $k_{off}$-Rate Assay To circumvent the exposure of the cysteine-containing peptide used to generate the data shown in FIG. 4 to the labeling mix, the UV-labile peptide was replaced after the labeling procedure in a UV-peptide exchange reaction, as depicted schematically in FIG. 10A. Thus, the cysteine in the peptide is expected to be unmodified.

Using the MHC monomers for multimerization on Strep-Tactin® and labeling TCR #1- and TCR #2-transduced T cells, a bright Streptamer® staining with high MHC multimer intensity and a dim MHC monomer intensity was observed (as is usually observed, due to quenching in the Streptamer complex; see FIG. 10B). Using these Streptamers, the cysteine-peptide specific TCR #1 and TCR #2 could be analyzed in the TCR ligand $K_{off}$-rate assay by flow cytometry; the results are shown in FIG. 10C. The dissociation half-life times calculated from the exponential decay curve fitted into the mean fluorescence intensities, shown in FIG. 10D, revealed a faster dissociation of 21 seconds for TCR #2 as compared to 51 seconds for TCR #1 indicating a different TCR avidity for the same target peptide MHC ligand.

Example 7

Development of a Labeling Procedure for Stable and Functional Ligands to Analyze Cell Surface Receptor—Ligand Interactions The methods provided herein allow the generation of stable, functional MHC ligands for TCRs with a strongly detectable label, which was not possible with previous labeling methods. To improve the stability of other ligands upon labeling, the method can be adapted to study a variety of other ligands modified with a non-natural occurring cysteine residue at a position not interfering with its structure and function.

In one embodiment, ligands that can be studied are adhesion molecules, which can be labeled using the disclosed methods; soluble, recombinantly expressed TCRs can then be used to measure binding of the adhesion molecules to their pMHC ligands. In another embodiment, the labeled adhesion molecules can be used to identify levels of expression of specific pMHC on the surface of target cell, and in yet another embodiment the labeled adhesion molecules can be used to query the binding and potential cross-reactivity towards similar pMHC expressed on cells such as healthy tissue cells (FIG. 11A).

The affinity of chimeric antigen receptors expressed on T cells mediates differences in their functionality (Hudecek et al., (2013) *Clin Cancer Res* 19(12):3153-64). Thus, in a further embodiment, recombinantly expressed, soluble antigenic proteins or immunogenic fragments of the protein will be labeled with the methods described herein to identify surface expressed chimeric antigen receptors (CARs) with optimal binding to their antigen mediating optimal target cell recognition (FIG. 11B, and as described in Nauerth et al., (2013) *Expert Rev Clin Immunol* 9(12):1151-53). In addition, scFv chains of the CARs labeled will be used to analyze the binding to antigen on the surface of the target cell or on tissue cells to query on- and off-target cross-reactivity (FIG. 11C). Labeling of invariant MHC monomers to identify surface expressed NK receptors will be performed using the disclosed methods (FIG. 11D).

Example 8

Measurement of Monomeric Receptor-Ligand Interactions

Co-localization of TCR and pMHC upon binding can be analyzed with another ligand, such as a specific scFv, labeled with the methods described herein that binds to a surface expressed molecule on the analyzed cell, preferably the TCR itself, CD3 or the co-receptor CD4/CD8. Fluorescence resonance energy transfer between the labels on the pMHC and the scFv can be analyzed as a measure for co-localization.

Depending on the strength of the interaction between surface expressed receptor and ligand labeled using the disclosed methods, the temperature during the acquisition can be adapted for different conditions, such as increased temperatures for high affinity ligands of about 20° C. to about 37° C. in the presence of buffer, yet allowing the binding event and inhibiting internalization of the ligand bound to the receptor. Representative conditions under which binding interactions can be studied include, for example, PBS containing 10% FCS, 1 mM EDTA, 0.01% azide or other inhibitors of internalization. Low affinity ligands may require immobilization, multimerization, high local concentrations, fixation of bound ligands by paraformaldehyde (PFA), and/or sensitive detection systems such as single molecule spectroscopy; ligands with higher affinity to their receptor/target such as CAR-ligands or Fab fragments can be used as monomers in titrated non-saturated and saturated concentrations.

Figure 12A:
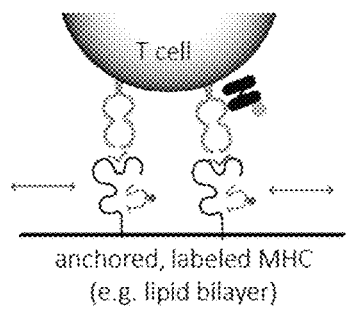
FIGS. 12A and 12B are a series of two cartoons depicting strategies to multimerize and immobilize detectably labeled, MHC monomers generated by the methods described herein.

Labeled pMHC ligands can be covalently or non-covalently immobilized to a surface of the experimental system by, e.g., reversible Strep-Tag®-Strep-Tactin®, $His_6$-tag Ni²⁺, and irreversible biotin-Streptavidin interaction. Further, the labeled pMHC ligands can be immobilized to other molecules such as phospholipids in a lipid bilayer as described in, for example, Ma et al., (2008) *PLoS Biol* 6(2):e43 and Huppa et al., (2010) *Nature* 463(7283):963-7. Thereby, labeled pMHC molecules will be able to move laterally in the lipid layer (FIG. 12A).

Figure 12B:
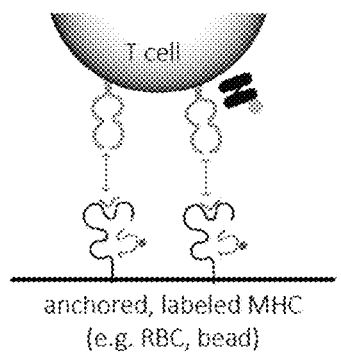

Another example of a suitable surface is a bead or a red blood cell that can be brought into close proximity of the T cell expressing the TCRs (FIG. 12B), e.g., by micropipette adhesion, and/or optical tweezers as described in, for example, Huang et al., (2010) *Nature* 464(7290):932-6; Zhang et al., (2016) *Sci Transl Med* 8(341):341ra77; Jiang et al., (2011) *Immunity* 34(1): 13-23; Jeorrett et al., (2014) *Opt Express* 22(2): 1372-80; Sabatino et al., (2011) *J Exp Med* 208(1):81-90; Pryshchep et al., (2014) *J Immunol* 193(1): 68-76; Liu et al., (2015) *Eur J Immunol* 45(7):2099-110; Adams et al., (2011) *Immunity* 35(5):681-93; Liu et al., (2014) *Cell* 157(2):357-68; Liu et al., (2014) *J Immunol* 44(1):239-50; Hong et al., (2015) *J Immunol* 195(8):3557-64; Casas et al., (2014) *Nat Commun* 5:5624. Other examples of analyzing two-dimensional kinetics are biological force probes, atomic force microscopy (AFM), flow chamber, microcantilever needle, centrifugation, rosetting, cone-plate viscometer, surface force apparatus, and fluorescence recovery after photobleaching (FRAP) (Long et al., (2006) *Cell Mol Immunol* 3(2):79-86; Bongrand (1999) *Rep Prog Phys* 62:921-68).

The soluble recombinantly expressed ligand, labeled with the methods described herein, can be applied to a physiological buffer through the device. An increased signal, such as photon emission by fluorescent dyes, upon binding to the receptor either expressed on the surface or immobilized on the device, can be detected. To analyze co-localization of TCR and pMHC upon binding, another ligand such as a scFv labeled with the methods described herein can be used.

Thus, an immobilization of T cells or other cells expressing the receptor, e.g., on a microfluidic device can be tested (FIG. 13A). While testing adherent cells is straightforward, examples of materials that can be useful for immobilizing suspension cells, such as T cells, is the usage of adhesion molecules (e.g., LFA), poly-L-lysine treated surface, DNA oligomer treated surfaces (see, e.g., Hennig et al., (2009) *Cytometry A:* 75(4):362-70), capture in di-electrophoretic cages (see, e.g., Muller et al., (2003) *IEEE Eng Med Biol Mag* 22(6):51-61; Forslund et al., (2012) *Front Immunol* 3:300), and others.

By analogy, either recombinantly expressed TCRs, or recombinantly expressed pMHC molecules can be covalently or non-covalently immobilized on the surface and tested for binding to their soluble ligands or ligands expressed on the surface of a cell (FIGS. 13B and C). Examples for the detection of a fluorescent label are different kinds of microscopy, such as fluorescence microscopy, confocal microscopy, total internal reflection microscopy. To quantify co-localization of receptor and labeled ligand, a FRET partner labeled with the disclosed methods can be used, such as a scFv.

Another example is a T cell captured with its labeled pMHC ligands in a vesicle consisting of a lipid bilayer as described for the interaction between single molecules in Ratzke et al., (2012) *J Mol Biol* 423(3):462-71. To analyze the weak interaction between a TCR and its ligand using MHC monomers labeled with the methods disclosed herein without previous reversible multimerization on, e.g., Strept-Tactin®, high local concentrations of the MHC monomer (e.g. in a small volume), a fixation of bound pMHC ligands by materials such as paraformaldehyde (PFA) can be used in order to measure $k_{on}$-rate kinetics, in analogy to previous methods using MHC multimers for measuring on-rate dynamics (Campanelli et al., (2002) *Int Immunol* 14(1):39-44; Dutoit et al., (2003) *J Immunol* 170(10):5110-7). To assess the equilibrium constant ($K_D$), titrated amounts of the MHC monomer ranging from non-saturating concentrations to saturating concentrations can be incubated with the T cells similar to MHC multimer based assays (Campanelli et al., (2002) *Int Immunol* 14(1):39-44; Dutoit et al., (2003) *J Immunol* 170(10):5110-7). Based on the label intensity (corrected for maximal intensity and/or TCR surface expression) T cells expressing optimal TCRs can be identified and isolated.

Example 9

Development of a High-Throughput Assay for the Identification of Peptides that Bind to a MHC Molecule In addition to the identification and characterization of T cells the MHC monomers labeled with the methods described herein and loaded with a UV-labile peptide can be used to screen peptide libraries derived from antigenic proteins for their ability to bind to the MHC. Algorithms such as SYFPEITHI (Rammensee et al., (1999) Immunogenetics 50:213-219 (access via syfpeithi.de)), NetMHC (Nielsen et al., (2003) Protein Sci. 12:1007-17; Andreatta & Nielsen, (2016) Bioinformatics 32(4):511-7 (access via cbs.dtu.dk/services/NetMHC)), and BIMAS (Parker et al. (1994) J Immunol. 152:163) can be used to identify peptides that bind to a specific MHC subtype. The algorithms are trained by experimental data and depending on the size of the data set, the false positive and/or false negative rate can increase. The UV-peptide exchange technology allows to rapidly screen peptide libraries for their binding to a specific MHC subtype in chromatography or an ELISA readout system measuring the amount of peptide loaded MHC after the exchange that correlates with the peptide binding affinity (Rodenko et al., (2006) Nat Protoc 1(3): 1120-32).

Figure 14:
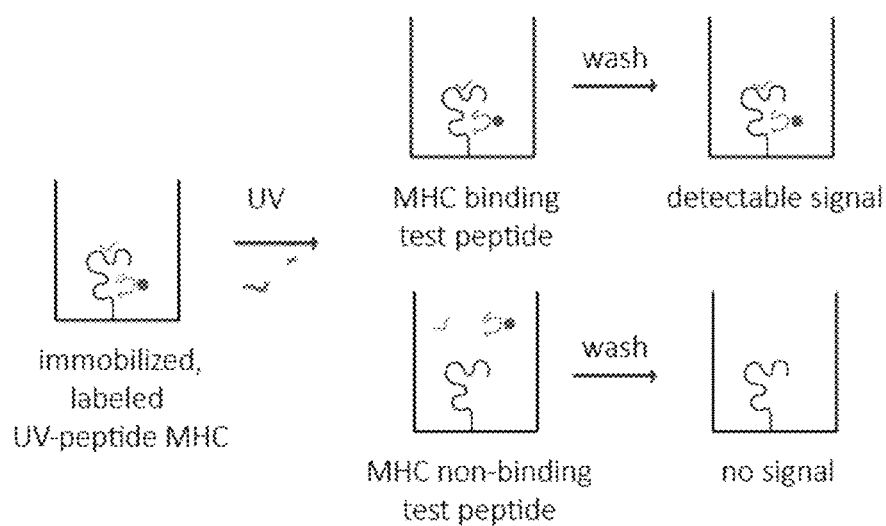
FIG. 14 is a cartoon depicting a high throughput method to identify antigenic peptides that bind to MHC monomers; the figure shows the UV-labile peptide loaded MHC labeled at the light chain with the methods described herein, immobilized in a well.
Figure 15:
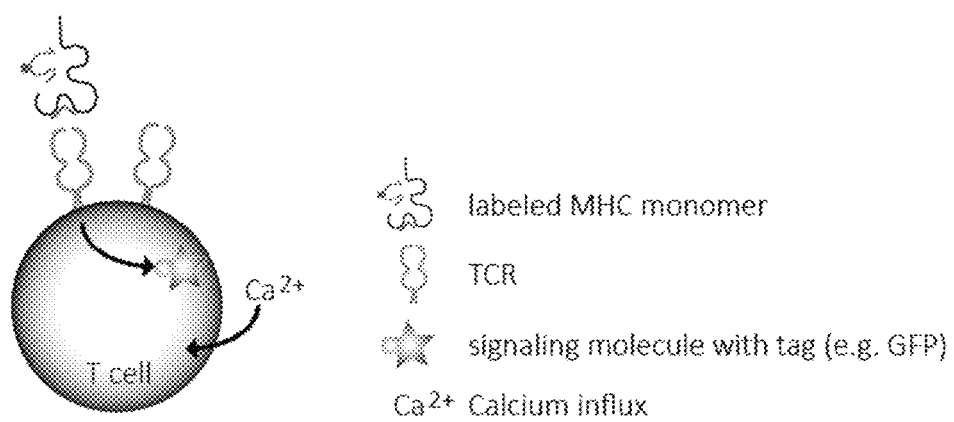
FIG. 15 is a cartoon depicting a strategy to simultaneously measure TCR ligand binding and T cell activation; the figure shows the TCRs expressed on the surface of a T cell, binding the labeled, soluble pMHC ligand and a labeled, intracellular signaling protein that is recruited to the activated TCR, as well as the calcium influx initiated upon activation of a T cell.

By using the UV-exchange peptide loaded MHC monomers labeled on the light chain using the methods disclosed herein, the amount of integrated MHC loaded with the test peptide can be easily quantified by measuring the signal of the label (FIG. 14).

In one embodiment, one test peptide is tested per well of a multi-welled plate and a cleavable (UV-labile) peptide loaded MHC is exposed to UV light in the presence of the test peptide. MHC incubated with peptides that do not bind will disintegrate into unassociated heavy and light chains; the labeled light chain and the peptide will be washed away. The signal of the label will correlate to the amount of assembled, labeled pMHC and therefore with the binding strength of the peptide to the MHC.

In addition to the assay based on quantifying the MHC monomers after UV-peptide exchange UV-peptide exchange (Rodenko et al., (2006) *Nat Protoc* 1(3):1120-32), other assays have been used to calculate the MHC stability as a readout for peptide binding to the MHC that can correlate to the immunogenicity of the pMHC for T cells (Harndahl et al., (2011) *J Immunol Methods* 374(1-2):5-12; Stronen et al., (2016) *Science* 352(6291):1337-41; Schmidt et al., (2017) *J Biol Chem* 292(28): 11840-11849).

Example 10

Parallel Measurement of TCR Ligand Binding and Downstream Activation Signals Correlating structural interaction between a TCR and its ligand to its potency to initiate downstream signaling for T cell activation is challenging to address. The MHC monomers generated using the disclosed methods can be used to analyze surface expressed TCRs. The measurement (e.g., MHC monomer association or dissociation) can be combined with a signaling readout. This can be achieved by modifying the T cell analyzed in signaling molecules with a reporter system. For example, a T cell can express a NFAT reporter system (see, e.g., Hamana et al., (2016) *Biochem Biophys Res Commun* 474(4):709-14) or a signaling molecule tagged with a detectable molecule that associates to the intracellular components of CD3 of activated TCR close to the cell surface (GFP tagged Zap70 in O'Donoghue et al., (2013) *Elife* 2:e00778). To analyze unmodified T cells, other functional readouts can be used in combination with measuring the TCR ligand interaction. For example, the upregulation of activation markers on the cell surface can be analyzed by labeled antibodies or Fabs in the buffer; or the production of effector molecules; or the calcium influx that is mediated quickly upon T cell activation measured by, e.g., Fura-2-acetoxymethyl ester. An example correlating structural TCR binding to a functional readout is described in Liu et al., (2014) *Cell* 157(2):357-68.

Example 11

Staining of T Cells for MHC-Peptide-TCR $k_{on}$-Rate Measurement

Combinatorial, irreversible MHC multimer staining was performed as previously described (Andersen et al., (2012) *Nat Protoc* 7(5): 891-902) using UV-exchanged, biotinylated HLA-A*02:01 molecules loaded with the same peptide and multimerized on Streptavidin BV421. Labeled, UV-exchanged peptide MHC monomers loaded with the peptide of interest were generated as described in the disclosed method in Example 1.

T cells were washed in PBS containing 10% BSA, EDTA and 0.09% azide at 4° C., and subsequently about 1*106 to 5*106 cells stained in the presence of anti-CD4 and/or anti-CD8 fluorescence conjugated antibodies, live-dead staining reagent and irreversible MHC multimer BV421 for 30 minutes and washed before analysis on the flow cytometer (BD Fortessa).

Example 12

TCR-Ligand $k_{on}$-Rate Measurement by Flow Cytometry

For each sample, $1 \times 10^4$ to $1 \times 10^5$ MHC multimer and antibody stained T cells were diluted into about 20-25° C. cold PBS, containing 10% BSA, EDTA, 0.09% azide, in a FACS microtube. The acquisition was started immediately after addition of 20 ul of the UV-exchanged peptide MHC monomer loaded with the peptide of interest to the sample tube (20 ul corresponds to ~16 uM) and MHC monomer association was followed for 2 min at room temperature (20-25° C.) (FIG. 16A). FACS data plots were analyzed using FLOWJO® by gating on CD4 negative, living lymphocytes and further on specific (irreversible MHC multimer positive) or unspecific (irreversible MHC multimer negative) T cells. Mean fluorescence intensities of the labeled pMHC monomer were exported over the time (FIG. 16B). Specific pMHC monomer association was calculated by subtracting the mean fluorescence intensities of unspecific T cells (irreversible MHC multimer negative) and the corrected data was plotted into Graph Pad Prism Software to fit an one-phase, non-linear association curve and calculate association half-life time (FIG. 16C). The association time for two TCRs specific for the identical peptide-MHC was monitored and compared to the association of the MHC monomer loaded with an unspecific, control peptide (FIG. 16D). Both TCRs have a distinct association time with a faster association time for TCR A (16s) as compared to TCR B (48s). In contrast, the control peptide loaded MHC monomers associated weakly with the TCRs.

---

What is claimed is:

1. A method of generating a detectably-labeled, soluble human MHC monomer loaded with a cleavable peptide, the method comprising:
   (a) obtaining a cleavable peptide that comprises one or more non-naturally occurring amino acids and that fits within a binding groove of a soluble human MHC monomer;
   (b) loading a soluble MHC monomer with the cleavable peptide by non-covalently associating the one or more non-naturally occurring amino acids of the cleavable peptide with the binding groove of the soluble human MHC monomer;
   (c) forming a labeling mixture comprising:
      (1) tris(2-carboxyethyl)phosphine (TCEP);
      (2) a maleimide-conjugated detectable label; and
      (3) a soluble MHC comprising an alpha chain and a beta chain, further comprising a non-naturally occurring cysteine residue, wherein the MHC is loaded with a cleavable peptide;
   (d) incubating the labeling mixture at a desired incubation temperature for a desired incubation period; and
   (e) removing unbound maleimide-conjugated detectable label from the labeling mixture.

2. The method of claim 1, wherein the label is selected from the group consisting of a radiolabel, fluorescent agents, chromogenic agents, chemiluminescent agents, and magnetic particles.

3. The method of claim 2, wherein the label is a fluorescent dye.

4. The method of claim 3, wherein the fluorescent dye is selected from the group consisting of an Atto dye, an Alexafluor dye, quantum dots, Hydroxycoumarin, Aminocoumarin, Methoxycoumarin, Cascade Blue, Pacific Blue, Pacific Orange, *Lucifer* yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry.

5. The method of claim 1, wherein the incubation period is about 2.5 hours or less and the incubation temperature is about 20-24° C.

6. The method of claim 1, wherein the incubation period is about 12 hours and the incubation temperature is about 4° C.

7. The method of claim 1, wherein the MHC is a MHC I.

8. The method of claim 7, wherein the non-naturally occurring cysteine is introduced at one or both of (a) position 67 or 88 of the MHC I beta chain; and (b) the C-terminus of the MHC I alpha chain.

9. The method of claim 1, wherein the MHC is a MHC II.

10. The method of claim 9, wherein the non-naturally occurring cysteine is introduced at one or both of (a) the C-terminus of the MHC II beta chain; and (b) the C-terminus of the MHC II alpha chain.

11. The method of claim 1, wherein the cleavable peptide is cleavable by UV light.

* * * * *